United States Patent
Rezach et al.

(10) Patent No.: US 9,204,909 B2
(45) Date of Patent: Dec. 8, 2015

(54) SPINAL ROD SYSTEM AND METHOD

(75) Inventors: William Alan Rezach, Atoka, TN (US); Jason May, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 352 days.

(21) Appl. No.: 13/182,149

(22) Filed: Jul. 13, 2011

(65) Prior Publication Data
US 2013/0018419 A1   Jan. 17, 2013

(51) Int. Cl.
*A61B 17/70* (2006.01)

(52) U.S. Cl.
CPC .......... *A61B 17/7076* (2013.01); *A61B 17/7085* (2013.01); *A61B 17/7086* (2013.01)

(58) Field of Classification Search
CPC ............. A61B 17/70; A61B 17/7074–17/7092
USPC .......... 606/86–89, 99, 246, 279; 81/448, 451, 81/453
See application file for complete search history.

(56) References Cited

U.S. PATENT DOCUMENTS

| | | | |
|---|---|---|---|
| 2,536,296 A | 1/1951 | Longfellow | |
| 5,720,751 A | 2/1998 | Jackson | |
| 6,083,225 A | 7/2000 | Winslow et al. | |
| 6,113,602 A | 9/2000 | Sand | |
| 6,183,472 B1 | 2/2001 | Lutz | |
| 6,746,454 B2 | 6/2004 | Winterbottom et al. | |
| 6,929,647 B2 | 8/2005 | Cohen | |
| 7,090,679 B2 | 8/2006 | Saint-Martin et al. | |
| 7,160,300 B2 | 1/2007 | Jackson | |
| 7,179,261 B2 | 2/2007 | Siecvol et al. | |
| 7,462,182 B2 | 12/2008 | Lim | |
| 7,465,306 B2 | 12/2008 | Pond, Jr. et al. | |
| 7,470,279 B2 | 12/2008 | Jackson | |
| 7,497,869 B2 | 3/2009 | Justis | |
| 7,575,581 B2 * | 8/2009 | Lovell | 606/104 |
| 7,651,502 B2 | 1/2010 | Jackson | |
| 7,758,584 B2 | 7/2010 | Bankoski et al. | |
| 7,815,644 B2 | 10/2010 | Masini | |
| 7,854,751 B2 | 12/2010 | Sicvol et al. | |
| 7,887,539 B2 | 2/2011 | Dunbar, Jr. et al. | |
| 7,887,541 B2 | 2/2011 | Runco et al. | |
| 7,918,857 B2 * | 4/2011 | Dziedzic et al. | 606/86 A |
| 7,918,858 B2 | 4/2011 | Stad et al. | |
| 7,922,731 B2 | 4/2011 | Schumacher et al. | |
| 7,931,673 B2 | 4/2011 | Hestad et al. | |
| 7,947,046 B2 | 5/2011 | Justis et al. | |
| 7,951,168 B2 | 5/2011 | Chao et al. | |
| 8,002,798 B2 | 8/2011 | Chin et al. | |
| 8,007,516 B2 | 8/2011 | Chao et al. | |
| 8,038,699 B2 * | 10/2011 | Cohen et al. | 606/246 |
| 8,048,129 B2 | 11/2011 | Forton et al. | |
| 2003/0149438 A1 | 8/2003 | Nichols et al. | |
| 2004/0249378 A1 | 12/2004 | Saint Martin et al. | |
| 2006/0089651 A1 | 4/2006 | Trudeau et al. | |
| 2006/0247658 A1 | 11/2006 | Pond, Jr. et al. | |
| 2006/0264942 A1 | 11/2006 | Lim et al. | |

(Continued)

*Primary Examiner* — Jan Christopher Merene
*Assistant Examiner* — Steven Cotroneo

(57) ABSTRACT

A spinal rod system includes a first instrument extending between a proximal portion and a distal portion along a longitudinal axis thereof. The proximal portion defines an inner cavity extending along the longitudinal axis. The first instrument includes a first arm extending along the longitudinal axis. The first arm defines a portion of a vertebral construct cavity disposed in communication with the inner cavity and includes a distal end being configured to engage a bone fastener. Methods of use are disclosed.

15 Claims, 20 Drawing Sheets

(56) References Cited

U.S. PATENT DOCUMENTS

| | | |
|---|---|---|
| 2007/0233155 A1* | 10/2007 | Lovell .................. 606/104 |
| 2007/0270867 A1 | 11/2007 | Miller et al. |
| 2008/0051794 A1 | 2/2008 | Dec et al. |
| 2008/0077138 A1 | 3/2008 | Cohen et al. |
| 2008/0091213 A1 | 4/2008 | Jackson |
| 2008/0125788 A1 | 5/2008 | Cohen et al. |
| 2008/0177269 A1 | 7/2008 | Seelig |
| 2008/0243190 A1 | 10/2008 | Dziedzic et al. |
| 2009/0030419 A1 | 1/2009 | Runco et al. |
| 2009/0143828 A1* | 6/2009 | Stad et al. ............. 606/86 A |
| 2009/0264930 A1 | 10/2009 | McBride |
| 2010/0042149 A1 | 2/2010 | Chao et al. |
| 2011/0015678 A1* | 1/2011 | Jackson .................. 606/264 |
| 2011/0022093 A1 | 1/2011 | Sherman et al. |
| 2011/0077690 A1 | 3/2011 | Shin et al. |
| 2011/0118791 A1 | 5/2011 | Numley et al. |
| 2011/0137358 A1 | 6/2011 | Manninen |
| 2011/0184469 A1 | 7/2011 | Ballard et al. |
| 2011/0257692 A1 | 10/2011 | Sandstrom et al. |
| 2011/0282402 A1 | 11/2011 | Chao et al. |

\* cited by examiner

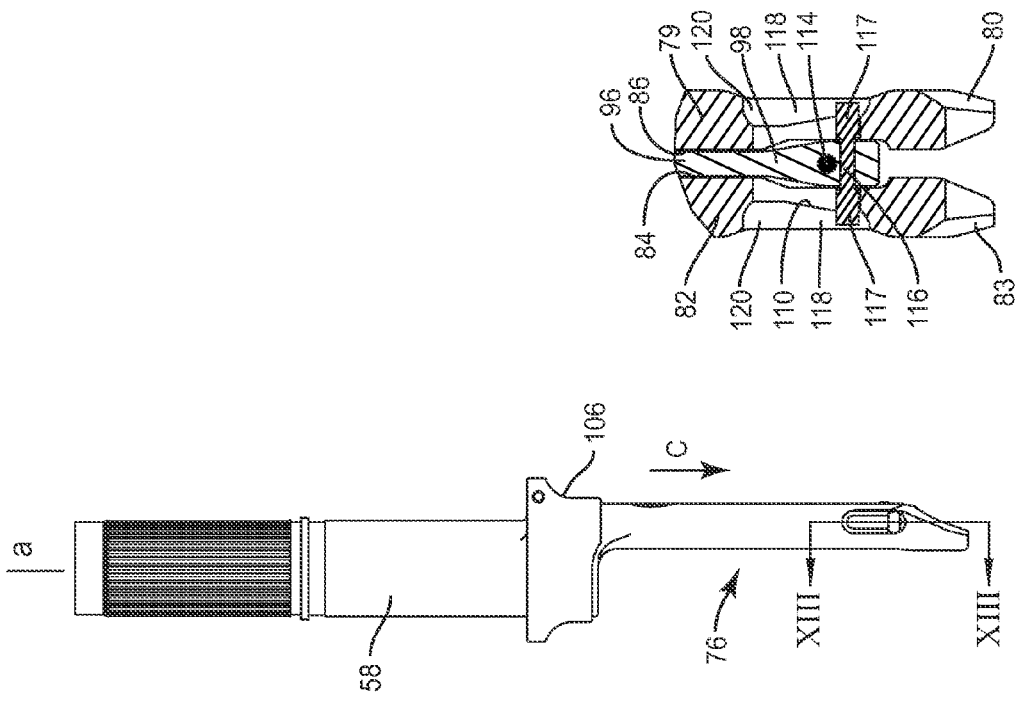
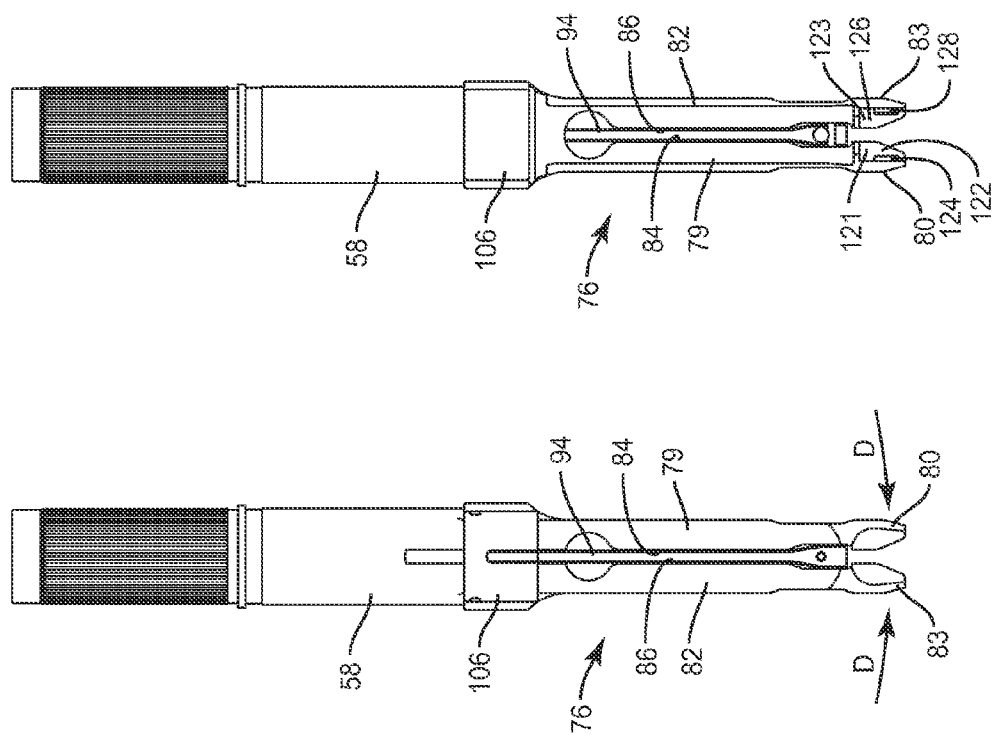

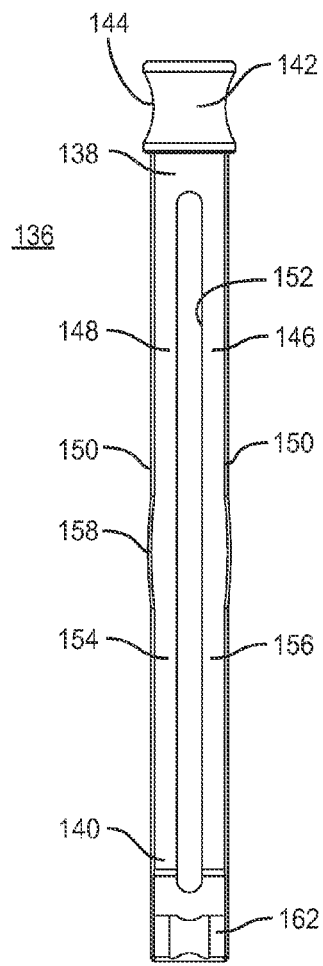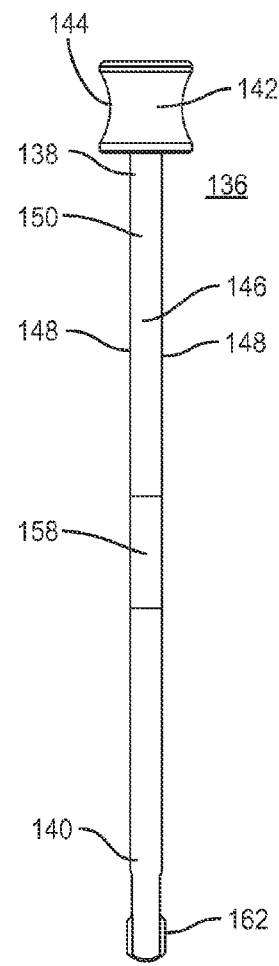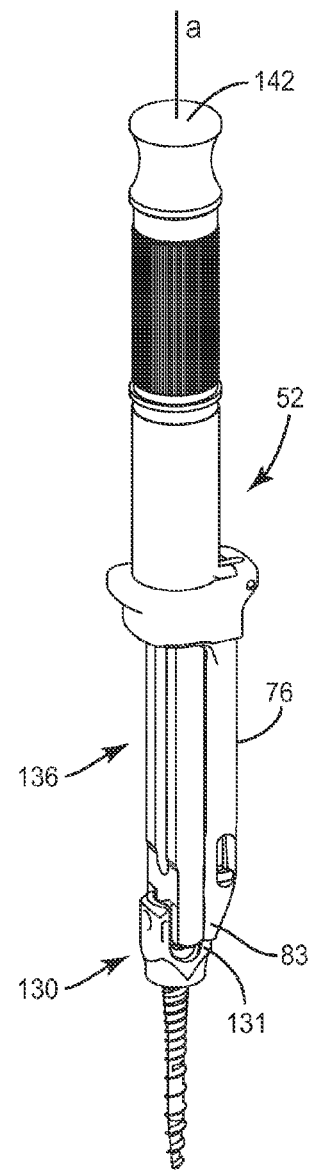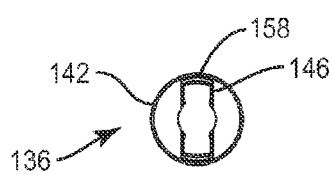
*FIG. 10*  *FIG. 11*  *FIG. 12*  *FIG. 13*

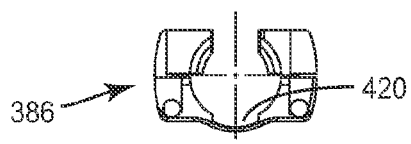
*FIG. 27*
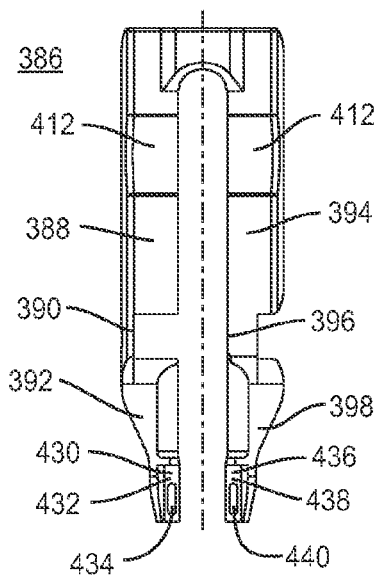 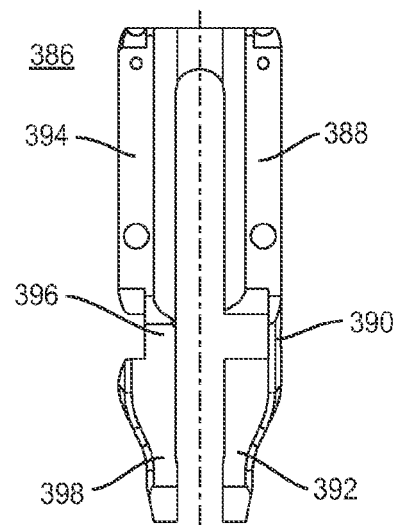 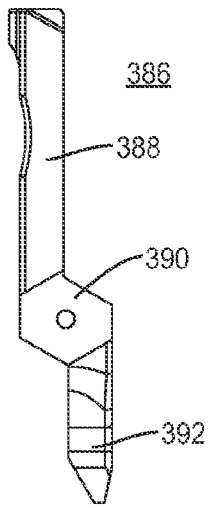
*FIG. 26*    *FIG. 28*    *FIG. 29*
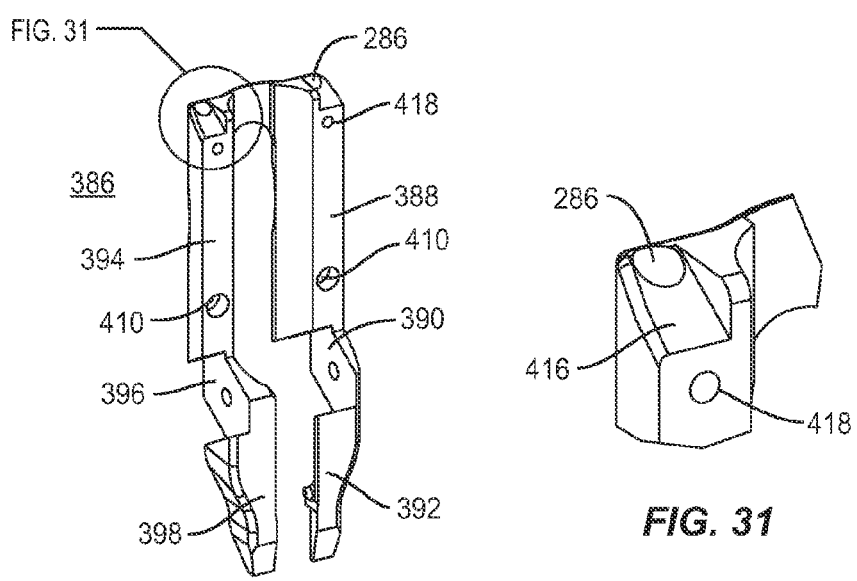
*FIG. 30*    *FIG. 31*

SPINAL ROD SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ rods and fasteners that are manipulated for engagement. This disclosure describes an improvement over these prior art technologies.

SUMMARY OF THE INVENTION

Accordingly, a surgical system is provided for implant delivery to a surgical site and a method for treating a spine. It is contemplated, for example, such delivery can include attachment of a vertebral rod to a bone anchor and reduction of the rod. It is further contemplated that the surgical system and method may be employed for scoliosis and kyphosis treatment.

In one particular embodiment, in accordance with the principles of the present disclosure, a spinal rod system is provided. The spinal rod system includes at least one first instrument extending between a proximal portion and a distal portion along a longitudinal axis thereof. The proximal portion defines an inner cavity extending along the longitudinal axis. The at least one first instrument includes at least one first arm extending along the longitudinal axis. The at least one first arm defines at least a portion of a vertebral construct cavity disposed in communication with the inner cavity and includes a distal end being configured to engage a bone fastener.

In one embodiment, the spinal rod system includes at least one first instrument extending along a longitudinal axis thereof and including a tubular proximal portion that defines an inner cavity and a distal portion that includes a first arm extending along the longitudinal axis and defining at least a portion of a vertebral construct cavity disposed in communication with the inner cavity. The first arm extends distally from the proximal portion and includes a first movable leg extension defining a distal engagement part and a second movable leg extension defining a distal engagement part. The leg extensions define an axial arm cavity. The at least one first instrument further includes a first actuator arm movable within the axial arm cavity along the longitudinal axis. The actuator arm is engageable with the leg extensions to cause the distal engagement parts to move in a direction transverse to the longitudinal axis between an open position and a closed position such that the distal engagement parts releasably capture a bone fastener. At least one second instrument extends between a proximal end and a distal end thereof. The at least one second instrument is disposable in the inner cavity such that the distal end of the at least one second instrument engages a bone fastener in a configuration to support the bone fastener with the distal engagement parts. At least one third instrument extends between a proximal end and a distal end thereof. The at least one third instrument is disposable in the inner cavity such that the distal end of the at least one third instrument is engageable with a vertebral construct disposed in the vertebral construct cavity in a configuration to move the vertebral construct into engagement with a bone fastener.

In one embodiment, the spinal rod system includes at least one bone fastener. An extender is disposed along a longitudinal axis thereof and includes a cylindrical proximal portion that defines an inner cavity having an inner surface and a distal portion that includes an arm extending along the longitudinal axis and defining at least a portion of a vertebral construct cavity disposed in communication with the inner cavity. The arm extends distally from the proximal portion and includes a first movable leg extension defining a distal engagement part and a second movable leg extension defining a distal engagement part. The leg extensions extend in a cantilevered configuration from the proximal portion and are oriented to define an axial arm cavity therebetween. The extender further includes an actuator arm axially movable within the axial arm cavity and a handle, connected with the actuator arm, which includes a grip surface configured to facilitate axial movement of the actuator arm. The actuator arm is engageable with the leg extensions to cause the distal engagement parts to move in a direction transverse to the longitudinal axis between an open position and a closed position such that the distal engagement parts releasably capture a bone fastener. An inserter extends between a proximal end and a distal end thereof. The inserter is slidably disposable in the inner cavity and along the inner surface such that the distal end of the inserter engages the at least one bone fastener in a configuration to support the at least one bone fastener with the distal engagement parts. A reducer extends between a proximal end and a distal end thereof. The reducer is disposable in the inner cavity and defines an outer threaded surface. The outer threaded surface engages the inner surface of the proximal portion of the extender to facilitate axial movement of the reducer relative to the extender such that the distal end of the reducer includes a pusher that is engageable with a vertebral construct disposed in the vertebral construct cavity in a configuration to move the vertebral construct into engagement with a bone fastener. The pusher is rotatable relative to the reducer and configured to engage the first arm to prevent rotation of the pusher relative to the at least one first arm.

BRIEF DESCRIPTION OF THE DRAWINGS

The present disclosure will become more readily apparent from the specific description accompanied by the following drawings, in which:

FIG. 5 is a side view of the first instrument shown in FIG. 1;

FIG. 6 is a side view of the first instrument shown in FIG. 1;

FIG. 7 is a front view of the first instrument shown in FIG. 1;

FIG. 8 is a section view of the first instrument shown along lines of FIG. 7;

FIG. 10 is a side view of one embodiment of a second instrument of a system in accordance with the principles of the present disclosure;

FIG. 11 is a front view of the second instrument shown in FIG. 10;

FIG. 12 is an end view of the second instrument shown in FIG. 10;

FIG. 13 is a perspective view of the first instrument shown in FIG. 1 engaged with the second instrument shown in FIG. 10 and a fastener;

FIG. 26 is a back view of a second arm of the first instrument shown in FIG. 20;

FIG. 27 is an end view of the second arm shown in FIG. 26;

FIG. 28 is a front view of the second arm shown in FIG. 26;

FIG. 29 is a side view of the second arm shown in FIG. 26;

FIG. 30 is a perspective view of the second arm shown in FIG. 26;

FIG. 31 is an enlarged detail view of the detail of the second arm shown in FIG. 30;

Like reference numerals indicate similar parts throughout the figures.

DETAILED DESCRIPTION OF THE INVENTION

Figure 1:
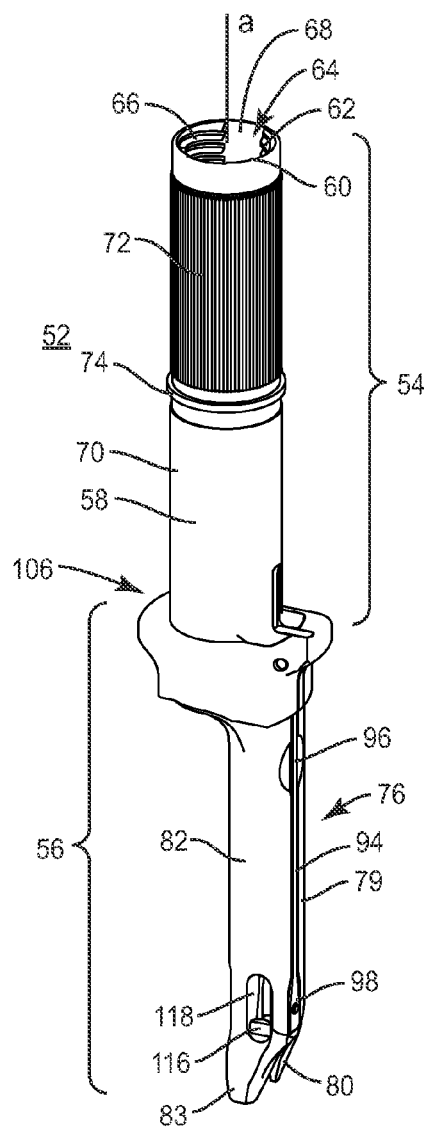
FIG. 1 is a perspective view of one particular embodiment of a first instrument of a system in accordance with the principles of the present disclosure.
Figure 2:
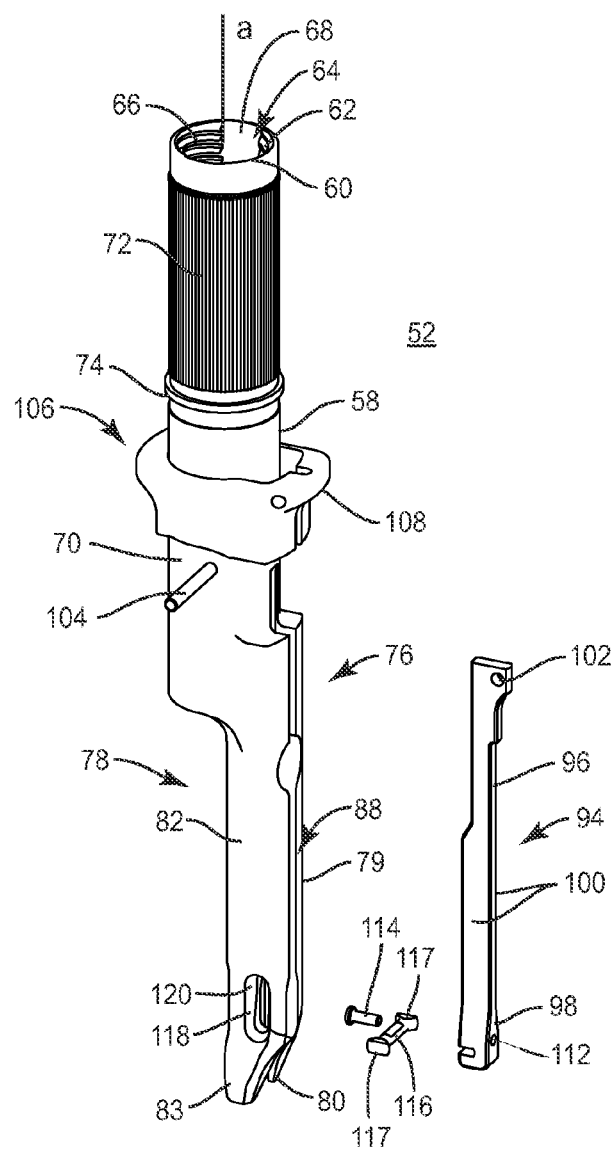
FIG. 2 is a perspective view of the first instrument shown in FIG. 1 with parts separated.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. It is envisioned that the surgical system can include an instrument system having extenders, reducers and translators, which can be used to introduce a vertebral construct such as a rod to a bone fastener such as a bone anchor or bone screw. For example, an extender can include bone anchor attachment features on one or both sides of the instrument. It is contemplated that the system may be used with a reducer assembly to introduce a rod into a bone fastener.

It is envisioned that the system may include instruments that are connected or attach to an extender(s) such as, for example, a lateral translation handle or derotaton instruments. It is further envisioned that the system may have an extender with a quick release mechanism to allow a reducer to slide into engagement with a rod. It is contemplated that the system can include an extender having features that prevent a rod and/or reducer assembly from rotating. In one embodiment, one or all of the components of the surgical system are disposable, peel-pack, pre-packed sterile devices used with an implant. One or all of the components of the surgical system may be reusable. The surgical system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-8, there is illustrated components of a surgical system, such as, for example, a spinal rod system in accordance with the principles of the present disclosure.

The components of the spinal rod system can be fabricated from biologically acceptable materials suitable for medical applications, including metals, synthetic polymers, ceramics and bone material and/or their composites, depending on the particular application and/or preference of a medical practitioner. For example, the components of the spinal rod system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the spinal rod system may have material composites, including the above materials, to achieve various desired characteristics such as strength, rigidity, elasticity, compliance, biomechanical performance, durability and radiolucency or imaging preference. The components of the spinal rod system, individually or collectively, may also be fabricated from a heterogeneous material such as a combination of two or more of the above-described materials. The components of the spinal rod system may be monolithically formed, integrally connected or include fastening elements and/or instruments, as described herein.

The spinal rod system is employed, for example, with an open or mini-open surgical technique to deliver and introduce an implant, such as, for example, a vertebral construct such as a rod to an implant, such as, for example, a bone fastener, at a surgical site within a body of a patient, for example, a section of a spine. In one embodiment, the components of the spinal rod system are configured to position the vertebral rod into engagement with the bone fastener for a correction treatment to treat various spine pathologies, such as, for example, adolescent idiopathic scoliosis and Scheuermann's kyphosis.

The spinal rod system includes a first instrument, such as, for example, an extender 52 that extends along a longitudinal axis a between a proximal portion 54 and a distal portion 56. Proximal portion 54 includes a tubular body 58 having a cylindrical cross-section configuration and a proximal opening 60. Body 58 extends axially from opening 60. It is contemplated that body 58 may extend from opening 60 in alternate configurations such as, for example, having a radius of curvature, offset and/or staggered. It is further contemplated that body 58 may extend at transverse orientations from opening 60, relative to longitudinal axis a, for example, perpendicular and/or other angular orientations such as acute or obtuse, co-axial and/or parallel.

Tubular body 58 includes an inner surface 62 that defines an inner cavity, such as, for example, a passageway 64. Inner surface 62 includes a threaded portion 66 and a smooth, non-threaded portion 68. Portions 66, 68 are each particularly configured for engagement with a particular instrument, as will be described. Body 58 is configured for disposal of surgical instruments to deliver one or more implants to a surgical site, as will be described. Body 58 includes an outer surface 70. Body 58 also includes a splined surface 72 and a retainer 74 that can be utilized for attachment of other instruments.

It is contemplated that the thickness defined by surfaces 62, 70 may be uniformly increasing or decreasing, or have alternate diameter dimensions along longitudinal axis a. It is further contemplated that all or only a portion of surfaces 62, 70 may have alternate surface configurations, such as, for example, rough, threaded for connection with surgical instruments, arcuate, undulating, porous, semi-porous, dimpled, polished and/or textured according to the requirements of a particular application. It is envisioned that body 58 may have alternate cross section configurations, such as, for example, oval, oblong, triangular, rectangular, square, polygonal, irregular, uniform, non-uniform, variable and/or tapered. It is further envisioned that body 58 may include fastening elements such as anchors, detents and/or openings for connection to surgical instruments.

Distal portion 56 includes an arm 76 extending along longitudinal axis a and defining at least a portion of a vertebral construct cavity, such as, for example, a rod slot 78 disposed in communication with passageway 64. Arm 76 extends distally in a linear orientation from body 58. It is contemplated that arm 76 may extend from body 58 in alternate configurations such as, for example, those alternatives described herein. It is further contemplated that arm 76 may extend at transverse orientations relative to longitudinal axis a, for example, perpendicular and/or other angular orientations such as acute or obtuse, co-axial and/or parallel.

Arm 76 includes a first movable leg extension 79 that defines a distal engagement part 80 and a second movable leg extension 82 that defines a distal engagement part 83. Leg extensions 79, 82 extend in a cantilevered configuration from body 58 and are flexible to facilitate movement relative to proximal portion 54 between a first position, such as, for example, an open position (FIG. 3) and a second position, such as, for example, a closed position (FIG. 5) such that parts 80, 83 engage a bone fastener, as will be described. The moving flexibility of leg extensions 79, 82 provide a resilient configuration such that extensions 79, 82 are biased to the closed position. It is contemplated that arm 76 may include one or a plurality of leg extensions. It is further contemplated that one or both of leg extensions 79, 82 may extend in alternate configurations and orientations, such as, for example, those alternatives described herein. It is envisioned that leg extensions 79, 82 may be pivotally movable.

Leg extensions 79, 82 include walls 84, 86, respectively, that are oriented to define an axial arm cavity 88 therebetween. Arm cavity 88 includes a proximal section 90 and a distal section 92. Arm cavity 88 is elongated and configured according to the configuration of walls 84, 86 and orientation of extensions 79, 82, as will be described.

Extender 52 includes an actuator arm 94 configured for slidable disposal within arm cavity 88. Actuator arm 94 is axially movable within arm cavity 88 to move leg extensions 79, 82 between the open and the closed positions. Actuator arm 94 has an elongated portion 96 and a distal head 98. Elongated portion 96 includes walls 100 that have a generally uniform configuration for slidable engagement with walls 84, 86. Distal head 98 is enlarged relative to elongated portion 96 and tapers distally to an increased width.

It is contemplated that the thickness of actuator arm 94 may be uniformly increasing or decreasing, or have alternate diameter dimensions along longitudinal axis a. It is further contemplated that all or only a portion of surfaces of actuator arm 94 may have alternate surface configurations, such as, for example, those alternatives described herein. It is envisioned that actuator arm 94 may have alternate cross section configurations, such as, for example, oval, oblong, triangular, rectangular, square, polygonal, irregular, uniform, non-uniform, variable and/or tapered.

Elongated portion 96 includes an aperture 102 that receives a pin 104 for connecting actuator arm 94 with a handle, such as, for example, an instrument release 106. Instrument release 106 has a grip surface 108 that is manipulable to facilitate axial movement of actuator arm 94 and thereby cause leg extensions 79, 82 to move. It is contemplated that all or only a portion of the surfaces of instrument release 106 may have alternate surface configurations, such as, for example, those alternatives described herein.

Figure 9:
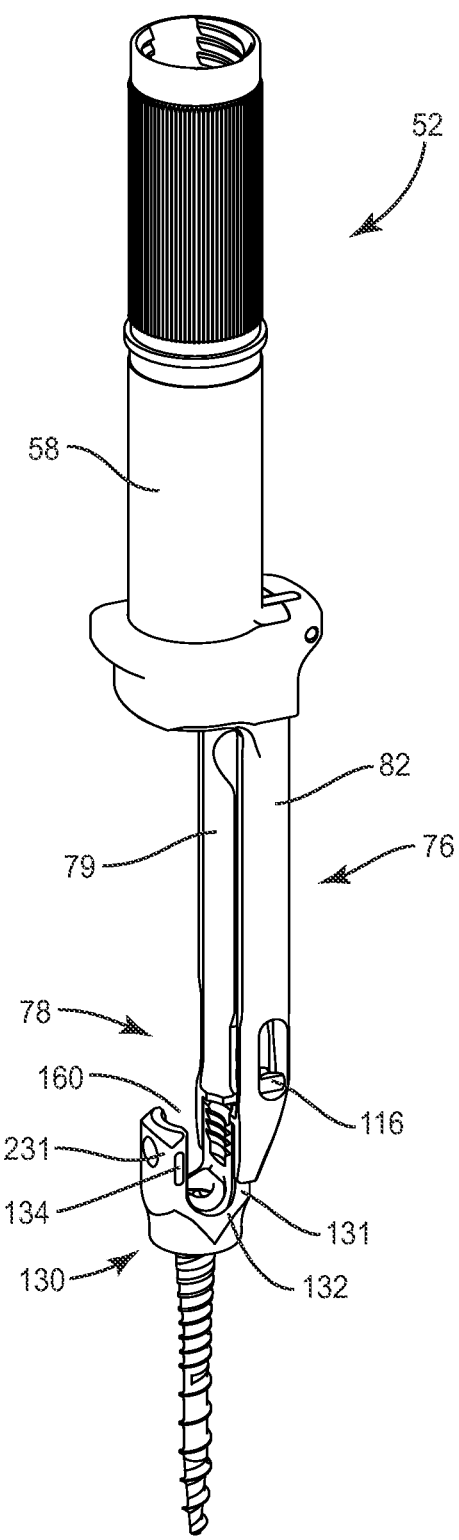
FIG. 9 is a perspective view of the first instrument shown in FIG. 1 engaged with a fastener.

Walls 84, 86 define a distal surface 110 having a tapered configuration for engaging distal head 98, as shown in FIG. 8. As the tapered configuration of distal head 98 slides along surface 110, engagement of their respective surfaces causes reciprocal and complimentary motion in leg extensions 79, 82 such that distal engagement parts 80, 83 move in a direction transverse to longitudinal axis a between the closed position and the opened position such that distal engagement parts 80, 83 are in an open state. In the closed state, the engagement parts 80, 83 releasably capture a bone fastener (FIG. 9).

Distal head 98 includes an aperture 112 that receives a pin 114 for connecting actuator arm 94 with leg extensions 79, 82. Pin 114 engages a slide 116, disposed in a slot of distal head 94, having a dogbone configuration with enlarged end portions 117. Enlarged end portions 117 are tapered and are configured to slidably engage tapered slots 118 of leg extensions 79, 82. Tapered slots 118 each include a tapered track surface 120 configured to engage enlarged end portions 117. Due to the described connection of distal head 98 with slide 116, enlarged end portions 117 slide along tapered track surfaces 120 such that engagement of their respective surfaces causes reciprocal and complimentary motion in leg extensions 79, 82 and distal engagement parts 80, 83. As such, slots 118 are configured to allow and limit movement of arm 94 and facilitate retention of distal engagement parts 80, 83 in the open and closed positions.

Distal engagement part 80 includes an engagement surface 121 for engaging and capturing a bone fastener, as shown in FIG. 6. Engagement surface 121 includes an arcuate surface 122 configured to contour and conform to a bone faster to facilitate attachment thereto. Engagement surface 121 includes a tab 124 that engages and is received by a complimentary cavity of a bone fastener to facilitate releasable fixation of extender 52 with a bone fastener.

Distal engagement part 83 includes an engagement surface 123 for engaging and capturing a bone fastener. Engagement surface 123 includes an arcuate surface 126 configured to contour and conform to a bone faster to facilitate attachment thereto. Engagement surface 123 includes a tab 128 that engages and is received by a complimentary cavity of a bone fastener to facilitate releasable fixation of extender 52 with a bone fastener. This configuration of extender 52 provides a single sided engagement with a bone fastener, as will be described. It is contemplated that all or only a portion of the engagement surfaces of distal engagement parts 80, 83 may have alternate surface configurations, such as, for example, those alternatives described herein. It is contemplated that the spinal rod system may include an extender that engages a bone fastener from one or a plurality of sides.

In operation of the spinal rod system, extender 52 is oriented for manipulation. Grip surface 108 is engaged and instrument release 106 is manipulated, in the direction shown by arrow A in FIG. 4, such that actuator arm 94 is slid proximally along longitudinal axis a. Distal head 98 slides along surface 110 proximally such that engagement of their respective surfaces causes reciprocal and complimentary motion in leg extensions 79, 82 in an outward direction transverse to longitudinal axis a, as shown by arrows B in FIG. 3, against the inward bias of leg extensions 79, 82.

Figure 3:
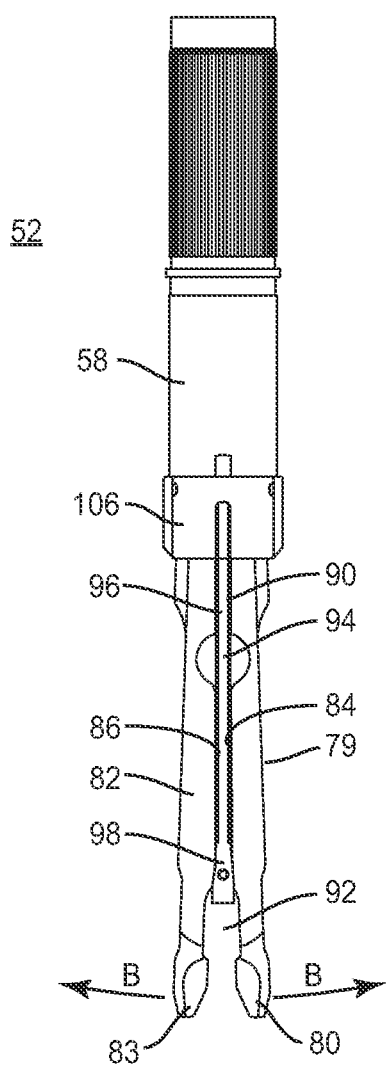
FIG. 3 is a side view of the first instrument shown in FIG. 1.
Figure 4:
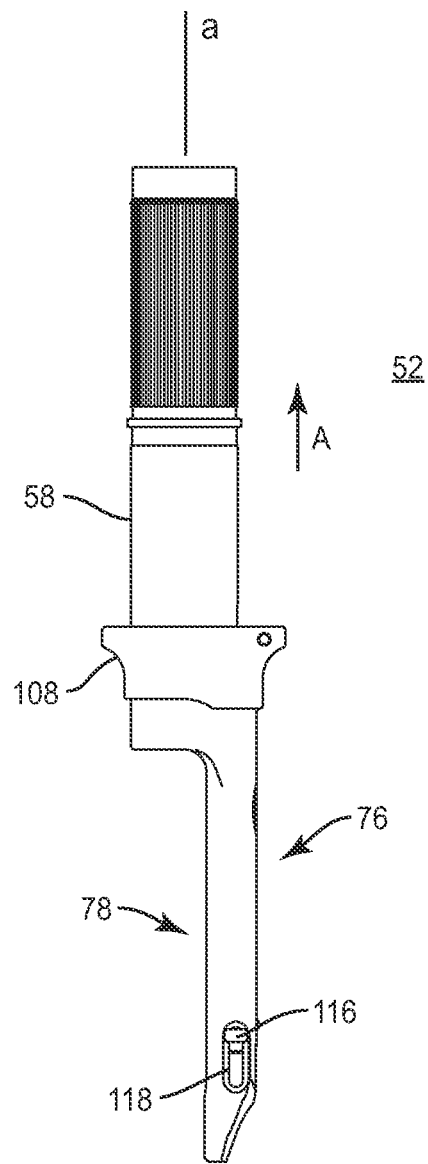
FIG. 4 is a front view of the first instrument shown in FIG. 1.

Slots 118 guide proximal movement of actuator arm 94 via engagement with slide 116. A proximal end of each of slots 118 provide a proximal movement limit for arm 94 as slide 116 engages such proximal end. Slide 116 is releasably fixed at the proximal movement limit due to the engagement of enlarged ends 117 with the configuration of track surface 120 adjacent the proximal end of slot 118. Distal engagement parts 80, 83 move outwardly and are disposed in the open position, as shown in FIG. 3.

Extender 52 is manipulated such that distal engagement parts 80, 83 are brought into close proximity with a head 132 of a bone fastener 130, as shown in FIG. 9. Engagement surfaces 121, 123 are aligned with a first extension 131 of head 132. Tabs 124, 128 are aligned with corresponding receiving cavities 134 of first extension 131 to provide a single sided engagement.

Grip surface 108 is engaged and instrument release 106 is manipulated, in the direction shown by arrow C in FIG. 7, such that actuator arm 94 is slid distally along longitudinal axis a. Distal head 98 slides along surface 110 distally such that engagement of their respective surfaces causes reciprocal and complimentary motion in leg extensions 79, 82 in an inward direction transverse to longitudinal axis a, as shown by arrows D in FIG. 5, via the inward bias of leg extensions 79, 82.

Slots 118 guide distal movement of actuator arm 94 via engagement with slide 116. Distal engagement parts 80, 83 move inwardly. A distal end of slots 118 provide a distal movement limit for actuator arm 94 as slide 116 engages such distal end. Tabs 124, 128 are received by cavities 134 of first extension 131 to capture bone fastener 130 in releasable fixation. Slide 116 is releasably fixed at the distal movement limit due to the engagement of enlarged ends 117 with the configuration of track surface 120 adjacent the distal end of slot 118. Distal engagement parts 80, 83 are disposed in the closed position, as shown in FIG. 5.

The spinal rod system includes a second instrument, such as, for example, an inserter 136, as shown in FIGS. 10-13, configured to align bone fastener 130 with arm 76. Inserter 136 extends between a proximal end 138 and a distal end 140. Inserter 136 is disposable in passageway 64 such that distal end 140 engages bone fastener 130 in a configuration to align bone fastener 130 with distal engagement parts 80, 83.

Proximal end 138 includes a handle, such as, for example, a removal knob 142 having a grip surface 144 configured to facilitate axial movement of inserter 136 within passageway 64 along longitudinal axis a. Removal knob 142 is manipulable to dispose inserter 136 within passageway 64.

Inserter 136 has an elongated body 146 defined by side walls 148 and end walls 150. Side walls 148 have a greater dimension than end walls 150 such that body 146 has a flattened bar configuration. Side walls 148 define an axial slot 152 such that body 146 includes a first arm 154 and a second arm 156. Slot 152 provides arms 154, 156 with a spring force and flexibility to facilitate to releasable engagement with non-threaded portion 68 of surface 62. End walls 150 include an enlarged portion, such as, for example, a bulge 158. Upon disposal of inserter 136 within passageway 64, bulge 158 is releasably engaged with non-threaded portion 68. Bulge 158, under the outward bias provided by arms 154, 156, is configured to interfere with non-threaded portion 68 to create a friction fit between extender 52 and inserter 136. It is contemplated that all or only a portion of body 146 may have various geometric configurations, such as, for example, those described herein.

Distal end 140 defines a profile configured to mate with a U-shaped channel 160 (FIG. 9) of bone fastener 130, as shown in FIG. 12. Upon capture of bone fastener 130 with distal engagement parts 80, 83, described above, inserter 136 is employed to secure bone fastener 130 with extender 52 for manipulation thereof at a surgical site.

Distal end 140 includes an enlarged portion 162 configured to engage the minor diameter of the threads in head 132 in a configuration to align bone fastener 130 with distal engagement parts 80, 83. Enlarged portion 162 forces first extension 131 into securement with distal engagement parts 80, 83 to grasp and hold bone fastener 130 for manipulation at a surgical site. Upon positioning and disposal of bone fastener 130, according to the requirements of an application, grip surface 144 of handle 142 is engaged to remove inserter 136 from passageway 64. As inserter 136 is drawn axially from passageway 64, the flexibility of arms 154, 156 allows bulge 158 to flex inwardly so that bulge 158 is released from the frictional fit engagement with non-threaded portion 68.

Figure 14:
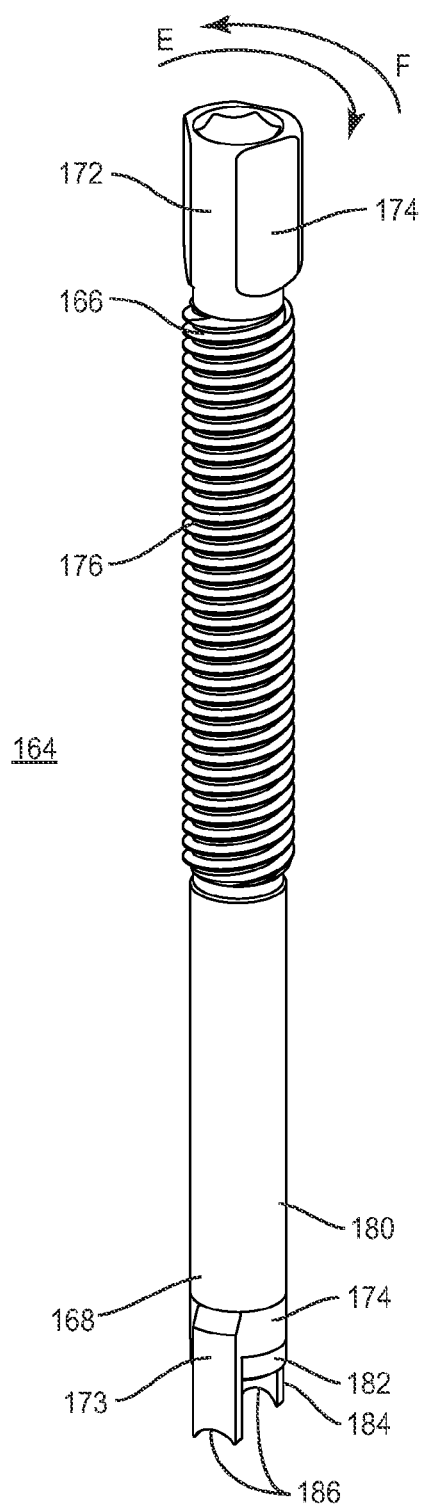
FIG. 14 is a perspective view of one embodiment of a third instrument of a system in accordance with the principles of the present disclosure.
Figure 15:
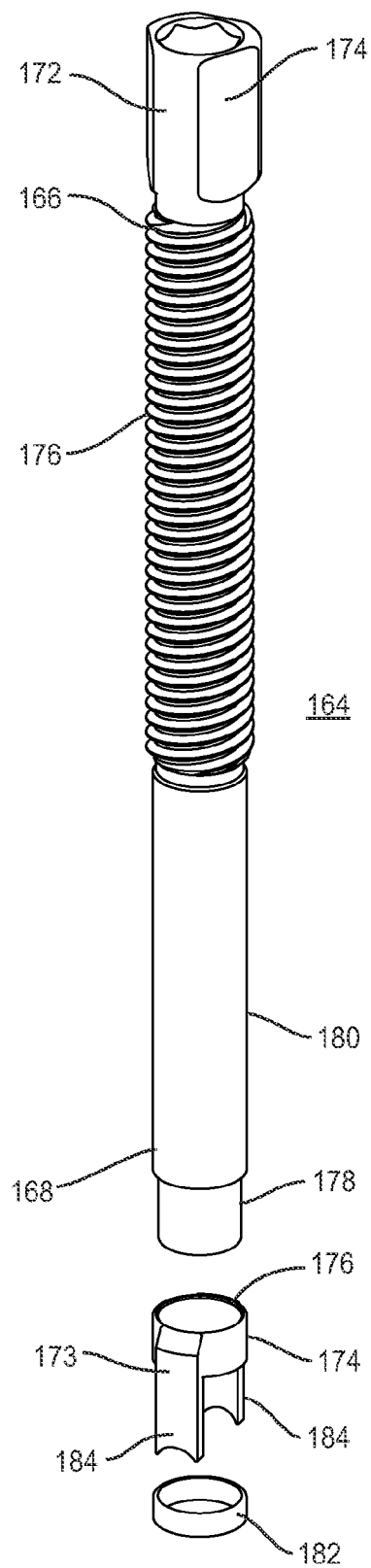
FIG. 15 is a perspective view of the third instrument shown in FIG. 14 with parts separated.

The spinal rod system includes a third instrument, such as, for example, a reducer 164, as shown in FIGS. 14-15. Reducer 164 extends between a proximal end 166 and a distal end 168. Proximal end 166 includes a handle 172 having a grip surface 174. Handle 172 is manipulable to align reducer 164 with passageway 64. Reducer 164 is disposable in passageway 64 and defines an outer threaded surface 176. Handle 172 is rotated such that surface 176 engages threaded portion 66 of surface 62 to facilitate axial translation of reducer 164 relative to extender 52 along longitudinal axis a.

Distal end 168 includes a pusher 173 that is engageable with a vertebral construct, such as, for example, a vertebral rod (not shown) configured for fixation with bone fastener 130 within U-shaped channel 160. Pusher 173 includes a cylindrical flange 174 that defines an aperture 176. Aperture 176 receives a reduced diameter portion 178 for mounting flange 174 with a non-threaded surface 180 of reducer 164. Range 174 is freely slidable about portion 178 such that pusher 173 is rotatable relative to surface 180. A retainer 182 is fixed with portion 178 to retain pusher 173 in the relatively rotatable configuration. Pusher 173 includes legs 184 having arcuate end surfaces 186 configured to engage the vertebral rod.

Upon positioning and fixation of bone fastener 130 within tissue at a surgical site, according to the requirements of an application, threaded surface 176 is aligned with threaded portion 66. Handle 172 is rotated, in the direction shown by arrows E in FIG. 14, to translate reducer 164 distally along longitudinal axis a relative to extender 52. Reducer 164 is translated such that arcuate end surfaces 186 engage the vertebral rod disposed in rod slot 78 in a configuration to move the vertebral rod distally into engagement with bone fastener 130.

Reducer 164 is further translated distally to drive the vertebral rod into U-shaped channel 160. As reducer 164 is rotated and translates axially, end surfaces 186 maintain alignment with U-shaped channel 160 and reducer 164 continues to rotate relative to pusher 173. As such, end surfaces 186 support the vertebral rod in a guided alignment with U-shaped channel 160. Although pusher 173 is rotatable relative to reducer 164, pusher 173 is configured to engage arm 76 to prevent rotation of pusher 173, and the vertebral rod, relative to arm 76. This configuration maintains alignment of the vertebral rod with U-shaped channel 160.

Handle 172 is manipulated to translate reducer 164 and drive the vertebral rod into U-shaped channel 160 for fixation with bone fastener 130, according to the requirements of a particular application. Handle 172 is rotatable, in the direction shown by arrows F in FIG. 14, to translate reducer 164 proximally such that reducer 164 is removed from extender 52. The vertebral rod can be fixedly secured with bone fastener 130 via a set screw (not shown) or similar securement. It is envisioned that the spinal rod system may include one or a plurality of extenders, inserters, reducers, bone fasteners and/or vertebral constructs, which may be alternately sized and dimensioned, and arranged as a kit, according to the requirements of a particular application.

Figure 16:
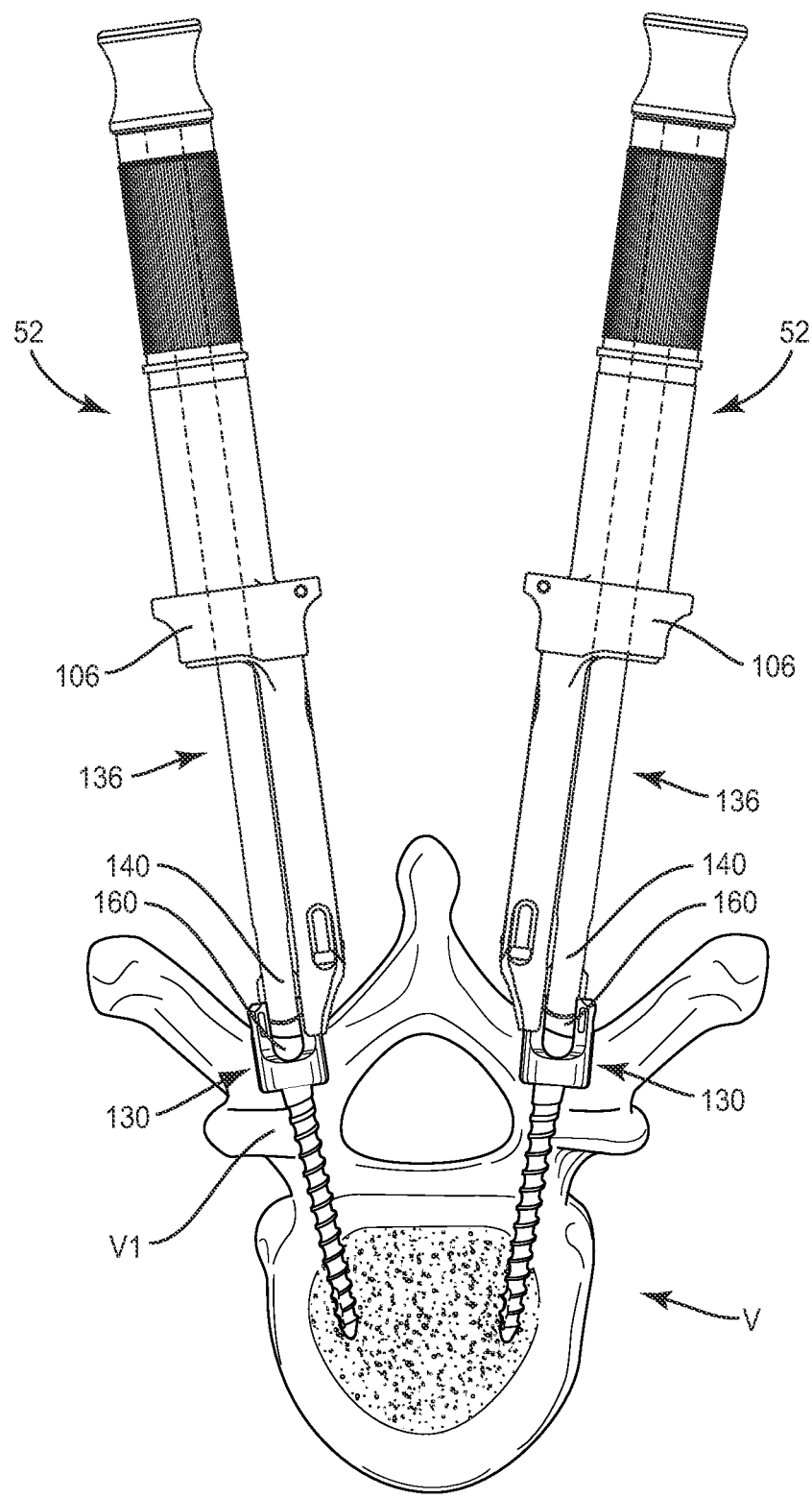
FIG. 16 is an axial view of a spine and a side view of a plurality of the first instrument shown in FIG. 1 and fasteners, and a plurality of the second instrument shown in FIG. 10.
Figure 17:
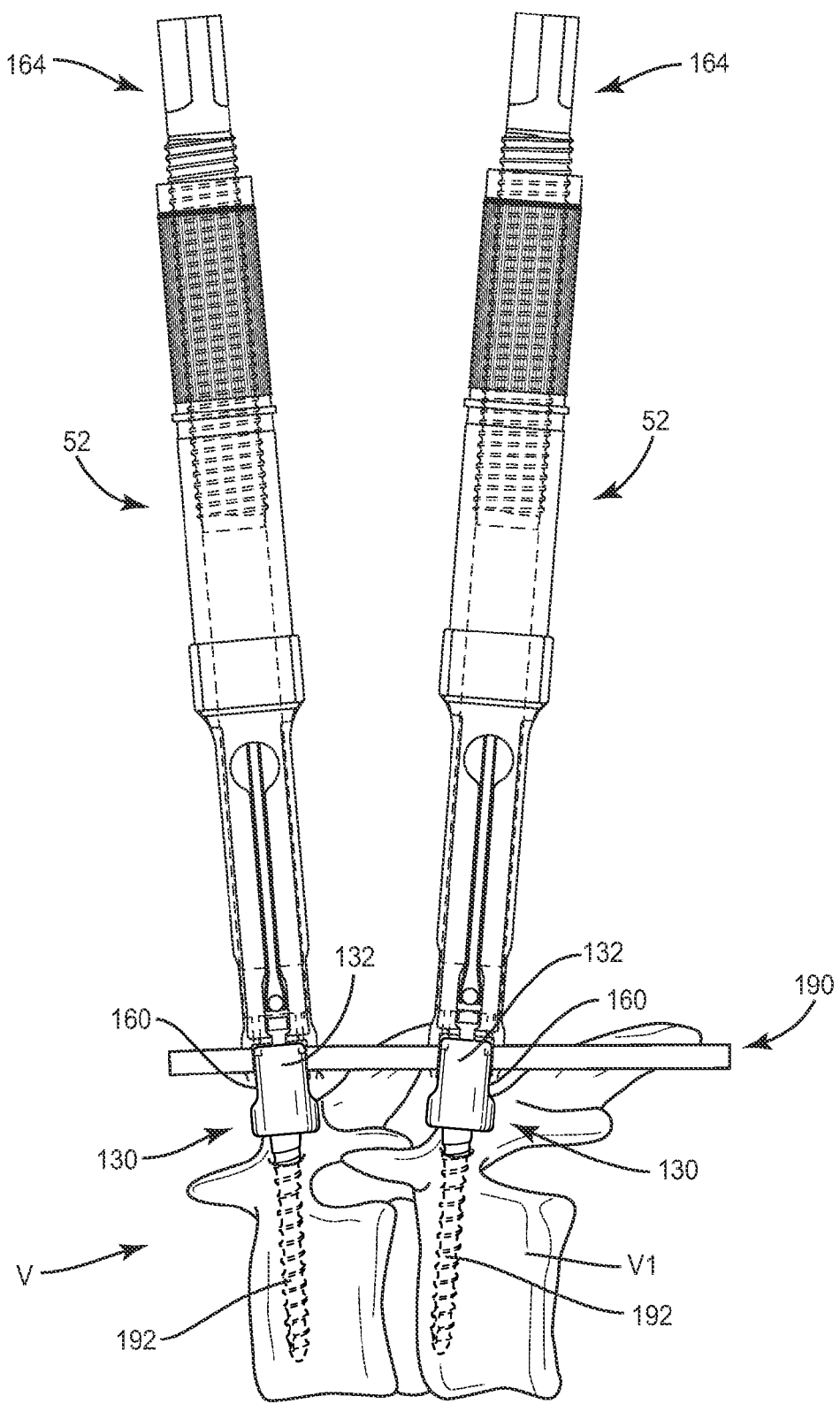
FIG. 17 is an oblique view of a section of the spine shown in FIG. 16 and a side view of a plurality of the first instrument shown in FIG. 1 and fasteners, and a plurality of the third instrument shown in FIG. 14 engaging a rod in phantom.

In assembly, operation and use, the spinal rod system is employed with a surgical procedure, in accordance with the principles of the present disclosure, for treatment of a spinal disorder affecting a section of a spine of a patient, as discussed herein. The spinal rod system is employed with a surgical procedure for treatment of a condition or injury of an affected section of the spine including vertebrae V, as shown in FIGS. 16-17, to provide support and maximize stabilization of vertebrae V.

In use, to treat the affected section of the spine, a medical practitioner obtains access to a surgical site including vertebra V in any appropriate manner, such as through incision and retraction of tissues in an open or mini-open surgical technique. It is envisioned that the spinal rod system may be used in any existing surgical method or technique including open surgery, mini-open surgery and minimally invasive surgery, whereby vertebrae V is accessed through a micro-incision, or sleeve that provides a protected passageway to the area. Once access to the surgical site is obtained, the particular surgical procedure is performed for treating the spinal disorder.

The spinal rod system, described with regard to FIGS. 1-15, including extender 52, inserter 136, reducer 164, bone fastener 130 and/or a vertebral rod 190 is then employed to augment the surgical treatment. For example, in one embodiment, the spinal rod system delivers and introduces implants, such as, for example, bone fastener 130 and vertebral rod 190 at the surgical site including vertebra V. In one embodiment, the components of the spinal rod system are configured to position vertebral rod 190 into engagement with bone fastener 130 for a correction treatment to treat adolescent idiopathic scoliosis and/or Scheuermann's kyphosis. It is contemplated that one or all of the components of the spinal rod system can be delivered or implanted as a pre-assembled device or can be assembled in situ. The spinal rod system may be completely or partially revised, removed or replaced.

Pilot holes (not shown) are made bilaterally in vertebrae V1 of vertebrae V for receiving bone fasteners 130. Extenders 52 are oriented for manipulation, alignment and capture of bone fasteners 130. Instrument release 106 of each extender 52 is manipulated (FIG. 4) to move leg extensions 79, 82 in an outward direction transverse to longitudinal axis a, (FIG. 3) such that distal engagement parts 80, 83 move outwardly and are disposed in the open position, as described above. Distal engagement parts 80, 83 are brought into close proximity with head 132 (FIG. 9) to align tabs 124, 128 with receiving cavities 134 of first extension 131 to provide a single sided engagement.

Instrument release 106 is manipulated such that leg extensions 79, 82 are moved inwardly (FIG. 7) and distal engagement parts 80, 83 are disposed in the closed position (FIG. 5). Tabs 124, 128 are received by cavities 134 of first extension 131 to capture bone fastener 130 in releasable fixation. As described above with regard to FIGS. 10-13, inserter 136 is disposed in passageway 64 such that distal end 140 engages bone fastener 130 in a configuration to support bone fastener 130 with distal engagement parts 80, 83, as shown in FIG. 16.

Distal end 140 mates with a U-shaped channel 160. Upon capture of bone fastener 130 with distal engagement parts 80, 83, described above, the assembled configuration of extender 52 and inserter 136 is employed to secure bone fastener 130 with extender 52 for manipulation thereof at a surgical site. Each assembled configuration of extender 52 and inserter 136 is manipulated to position bone fastener 130 with a respective pilot hole in vertebrae V1 at the surgical site. Thereafter, handle 142 is engaged to remove inserter 136 from passageway 64, as described.

Threaded bone engaging portion 192 of each bone fastener 130 is inserted, drilled or otherwise fixed to vertebrae V1. Handle 172 is manipulable to align reducer 164 with passageway 64, as described above with regard to FIGS. 14 and 15, and rotated to translate reducer 164 distally relative to extender 52. Reducer 164 is translated such that end surfaces 186 engage vertebral rod 190 disposed in rod slot 78 in a configuration to move vertebral rod 190 distally to drive vertebral rod 190 into U-shaped channel 160. As reducer 164 is rotated and translates axially, end surfaces 186 maintain alignment with U-shaped channel 160 and reducer 164 continues to rotate relative to pusher 173. As such, end surfaces 186 support vertebral rod 190 in a guided alignment with U-shaped channel 160. Handle 172 is manipulated to translate reducer 164 and drive vertebral rod 190 into U-shaped channel 160 for fixation with bone fastener 130.

Reducer 164 is translated proximally for removal from extender 52. Vertebral rod 190 is fixedly secured with bone fastener 130 via a set screw (not shown) torqued onto to head 132. Upon completion of the procedure, the surgical instruments and assemblies are removed and the incision is closed. It is envisioned that bone fastener 130 may be employed as a bone screw, pedicle screw or multi-axial screw (MAS) used in spinal surgery.

In one embodiment, the spinal rod system may include fastening elements, which may include locking structure, for assembling, attaching or connecting the instruments. It is envisioned that locking structure may include fastening elements such as, for example, clips, hooks, adhesives and/or flanges. The components of the spinal rod system can be made of radiolucent materials such as polymers. Radiomarkers may be included for identification under x-ray, fluoroscopy, CT or other imaging techniques. It is envisioned that the use of micro surgical and image guided technologies may be employed to access, view and repair spinal deterioration or damage, with the aid of the spinal rod system.

It is envisioned that bone fasteners 130, vertebral rod 190 and/or other implants of the spinal rod system may be coated with biocompatible materials such as an osteoconductive material such as (HA)-TCP and/or osteoinductive agent such as a bone morphogenic protein (BMP) for enhanced bony fixation. It is envisioned that the biocompatible material and/or an agent employed with an implant of the spinal rod system may include one or more therapeutic agent(s) disposed in one or more layers or homogenously throughout it. For example, an implant of the spinal rod system may include at least one agent including biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as (HA)-TCP, calcium phosphate and calcium sulfite. It is further envisioned that such an implant may include biologically active agents, for example, biologically active agents coated onto the exterior of the implant and/or applied thereto for gradual release such as by blending in a bioresorbable polymer that releases the biologically active agent or agents in an appropriate time dependent fashion as the polymer degrades within the patient.

Figure 18:
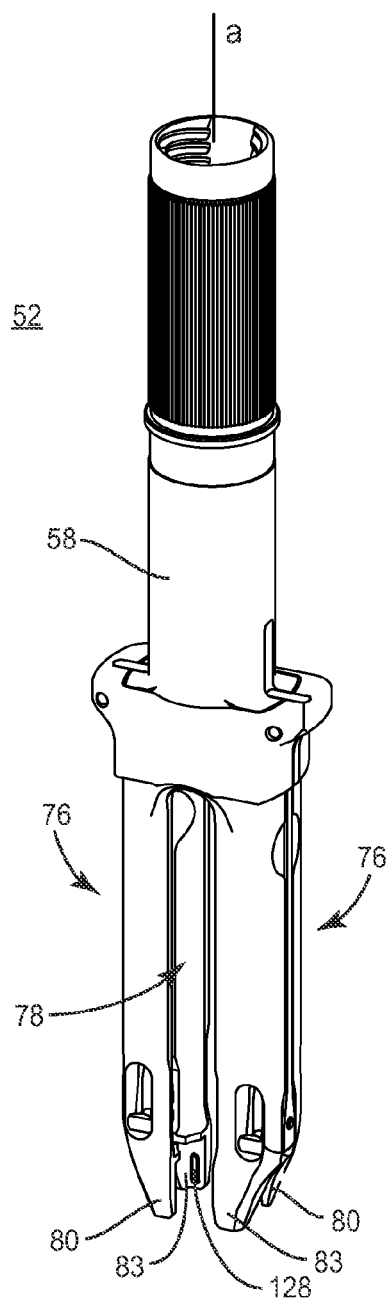
FIG. 18 is a perspective view of one embodiment of the first instrument shown in FIG. 1.
Figure 19:
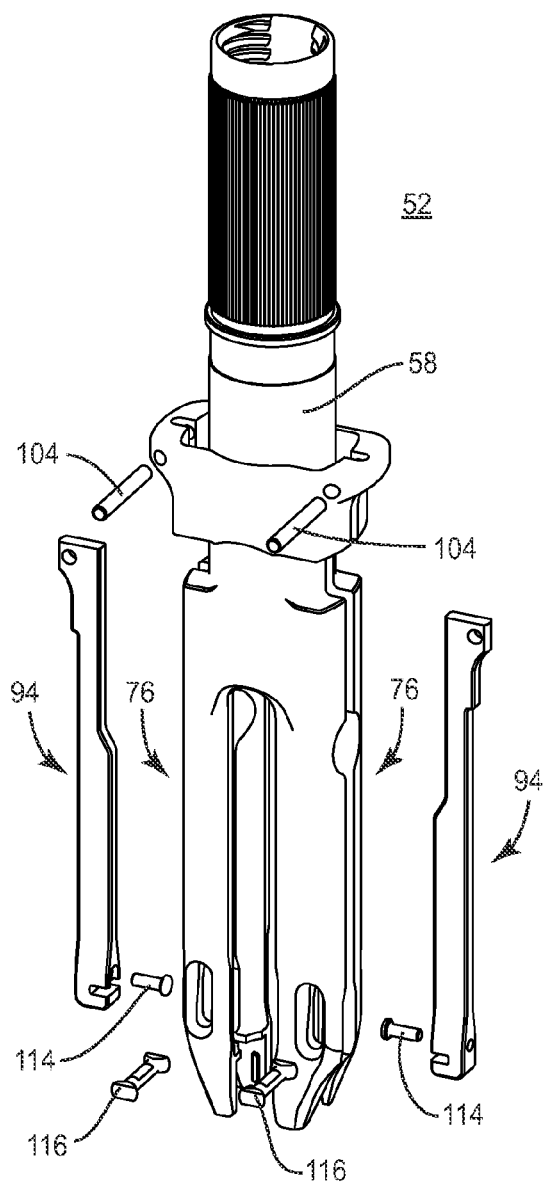
FIG. 19 is a perspective view of the first instrument shown in FIG. 18 with parts separated.

In one embodiment, as shown in FIGS. 18 and 19, the spinal rod system, described above, includes a pair of opposing arms 76, each arm 76 being described in structure and operation with regard to FIGS. 1-17. Opposing arms 76 extend uniformly and in parallel, along longitudinal axis a. Opposing arms 76 extend distally in a linear orientation from body 58 to define rod slot 78. Each of arms 76 includes distal engagement parts 80, 83, described above. The engagement surfaces of distal engagement parts 80, 83 for each of arms 76 are aligned with first extension 131 and a second extension 231 of head 132 (FIG. 9) in a configuration for disposal circumferentially about bone fastener 130. Tabs 124, 128 are aligned with corresponding receiving cavities 134 of extensions 131, 231 to provide a dual sided engagement. Tabs 124 are received by cavities 134 of extensions 131, 231 such that extender 52 surrounds and captures bone fastener 130 in a releasable fixation. It is envisioned that extender 52 may include one or a plurality of arms 76 extending therefrom, variously disposed about longitudinal axis a.

In one embodiment, as shown in FIGS. 20-38, the spinal rod system, similar to that described above, includes a first instrument, such as, for example, an extender 252 that extends along a longitudinal axis a between a proximal portion 254 and a distal portion 256. Proximal portion 254 includes a tubular body 258 having a cylindrical cross-section configuration and a proximal opening 260. Body 258 extends axially from opening 260. It is contemplated that body 258 may extend from opening 260 in alternate configurations such as, for example, those alternatives described herein. It is further contemplated that body 258 may extend at transverse orientations from opening 260, relative to longitudinal axis a, for example, perpendicular and/or other angular orientations such as acute or obtuse, co-axial and/or parallel.

Tubular body 258 includes an inner surface 262 that defines an inner cavity, such as, for example, a passageway 264. Inner surface 262 includes a smooth bore 266 and a groove 268. Body 258 is configured for disposal of surgical instruments to deliver one or more implants to a surgical site, as will be described. Body 258 includes an outer surface 270. A quick release handle 272 is mounted to outer surface 270 for engaging and releasing a reducer 264, described below. Quick release handle 272 allows for selective engagement and disengagement of reducer 264. With quick release handle 272 disengaged, reducer 264 is slidable proximally and distally. With quick release handle 272 engaged, reducer 264 is threaded to provide mechanical advantage to reduce a rod into a bone screw head. Quick release handle 272 can be spring loaded to allow for automatic engagement with the thread, but when depressed it disengages the thread allowing for sliding of the reducer. Threads of reducer 464 engage quick release handle 272 to facilitate translation of reducer 464 relative to extender 252, as will be described. Handle 272 includes a button 273 that extends through an opening 275 defined in body 258 and into passageway 264. Button 273 is depressed to adjust position of reducer 464 and disengage reducer 464 from the threads of reducer 464. Actuation of handle 272 allows reducer 464 to slide freely into engagement with a vertebral construct. Inner surface 262 includes a relief 261, configured as a cutout or interruption in inner surface 262, that facilitates loading of reducer 464 through opening 260.

It is contemplated that the thickness defined by surfaces 262, 270 may be uniformly increasing or decreasing, or have alternate diameter dimensions along longitudinal axis a. It is further contemplated that all or only a portion of surfaces 262, 270 may have alternate surface configurations, such as, for example, those alternatives described herein. It is envisioned that body 258 may have alternate cross section configurations, such as, for example, those alternatives described herein. It is further envisioned that body 258 may include fastening elements such as anchors, detents and/or openings for connection to surgical instruments.

Distal portion 256 includes a first arm, such as, for example a stationary arm 276 extending along longitudinal axis a and defining at least a portion of a rod slot 278 disposed in communication with passageway 264. Stationary arm 276 extends distally in a linear orientation from body 258. It is contemplated that stationary arm 276 may extend from body 258 in alternate configurations such as, for example, those alternatives described herein. It is further contemplated that stationary arm 276 may extend at transverse orientations relative to longitudinal axis a, for example, perpendicular and/or other angular orientations such as acute or obtuse, co-axial and/or parallel.

Stationary arm 276 includes a first leg extension 279 that extends to a hinge connection portion 380 and defines a distal engagement part 280. Stationary arm 276 includes a second leg extension 282 that extends a hinge connection portion 382 and defines a distal engagement part 283. It is contemplated that leg extensions 279, 282 may be flexible, jointed and/or articulating.

Stationary arm 276 defines a recess 384 configured for movable disposal of a second arm, such as, for example, a pivoting arm 386 of extender 252. Pivoting arm 386 includes a first leg extension 388 that extends to a hinge connection portion 390 and defines a distal engagement part 392. Pivoting arm 386 includes a second leg extension 394 that extends to a hinge connection portion 396 and defines a distal engagement part 398. It is contemplated that leg extensions 388, 394 may be flexible, jointed and/or articulating.

Stationary arm 276 is attached to pivoting arm 386 at hinge connection portions 390, 396. Pivoting arm 386 is pivotable relative to stationary arm 276 such that pivoting arm 386 rotates to surround and capture bone fastener 130 with stationary arm 276 in a releasable fixation to provide a dual sided engagement. Pivoting arm 386 is pivotable to a closed position (FIG. 21) such that leg extensions 388, 394 and distal engagement parts 392, 398 rotate in the direction shown by arrows AA in FIG. 21. Leg extensions 388, 394 and distal engagement parts 392, 398, rotate about hinge connection portions 390, 396 and relative to stationary arm 276 such that distal engagement parts 392, 398 surround and capture bone fastener 130 with distal engagement parts 280, 283 in a releasable fixation to provide a dual sided engagement.

Figure 20:
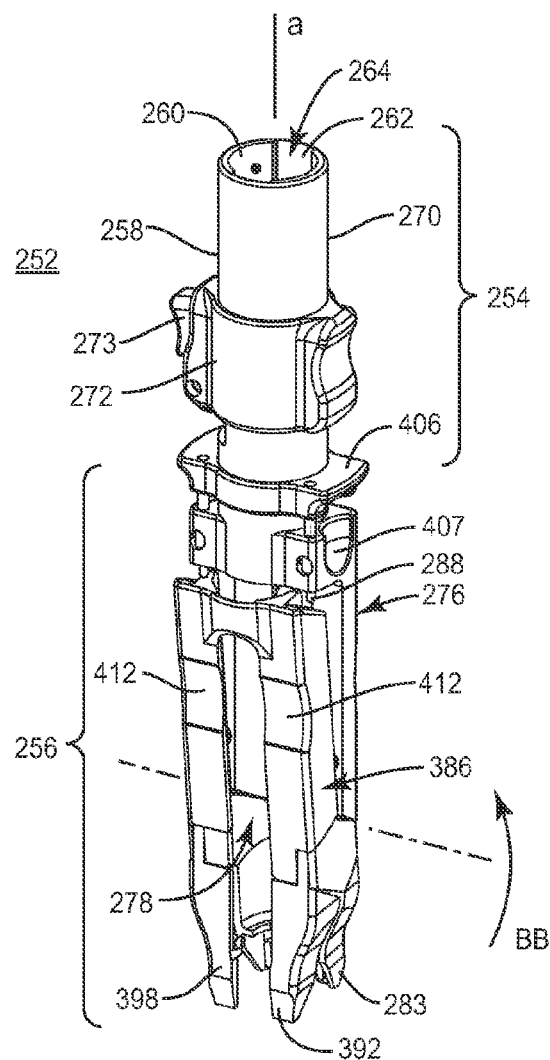
FIG. 20 is a perspective view of one embodiment of the first instrument shown in FIG. 1.

Pivoting arm 386 is pivotable to an open position (FIG. 20) such that leg extensions 388, 394 and distal engagement parts 392, 398, rotate in the direction shown by arrows BB in FIG. 20. Leg extensions 388, 394 and distal engagement parts 392, 398, rotate about hinge connection portions 390, 396 and relative to stationary arm 276 such that distal engagement parts 392, 398 and 280, 283 release bone fastener 130.

To facilitate pivotal movement of pivoting arm 386 and rotation of pivoting arm 386 relative to stationary arm 276, stationary arm 276 includes retaining bores 284 and pivoting arm 386 includes retaining bores 286 that receive retainers 288. Retainers 288 connect stationary arm 276 with pivoting arm 284 to prevent pivoting of pivoting arm 386 relative to stationary arm 276. Retainers 288 include biasing members, such as, for example, springs for a spring loaded configuration with an instrument release 406. Instrument release 406 is manipulable axially to dispose stationary arm 276 and pivoting arm 284 in the open and closed positions. Grooves 407 facilitate access to and manipulation of instrument release 406 between the open and closed positions.

To facilitate pivotal movement of pivoting arm 386 and rotation of pivoting arm 386 relative to stationary arm 276, stationary arm 276 includes spring bores 408 and pivoting arm 386 includes spring bores 410 that support biasing members, such as, for example, springs (not shown). The springs are configured to facilitate rotation of pivoting arm 386 via engagement therewith. Pivoting arm 386 includes grooves 412 and stationary arm 276 includes grooves 414 that are manipulable to dispose stationary arm 276 and pivoting arm 386 in the closed position. As grooves 412, 414 are manipulated to close pivoting arm 386, retainers 288 engage cam surfaces 416 of pivoting arm 386 to actuate retainers 288 and the springs disposed in bores 408, 410. Pivoting arm 386 includes a sterilization and cleaning port 418. Pivoting arm 386 includes a relief 420 that facilitates loading of reducer 264, similar to relief 261 described above.

Figure 21:
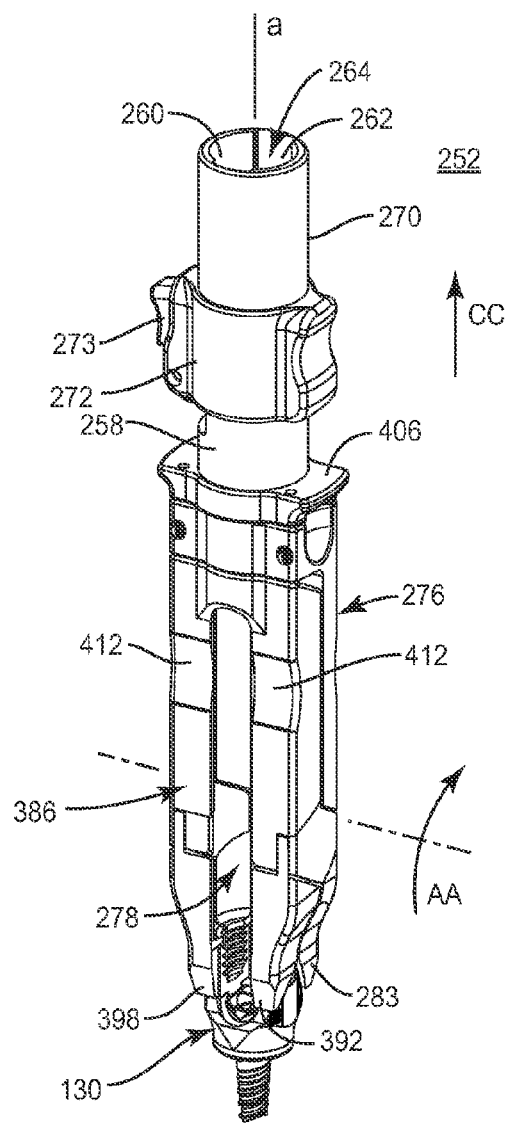
FIG. 21 is a perspective view of the first instrument shown in FIG. 20 engaged with a fastener.
Figure 22:
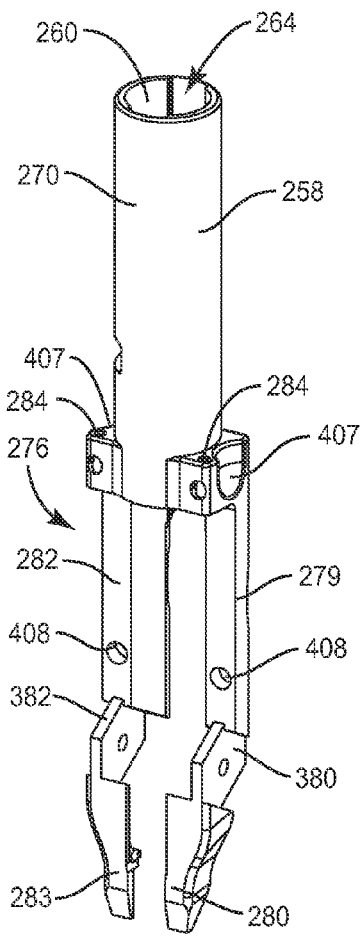
FIG. 22 is a perspective view of a first arm of the first instrument shown in FIG. 20.
Figure 24:
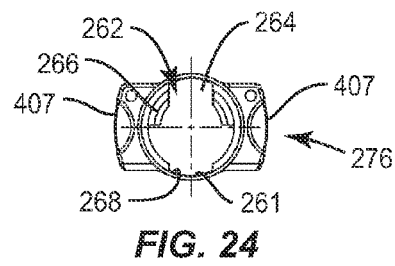
FIG. 24 is an end view of the first arm shown in FIG. 22.
Figure 23:
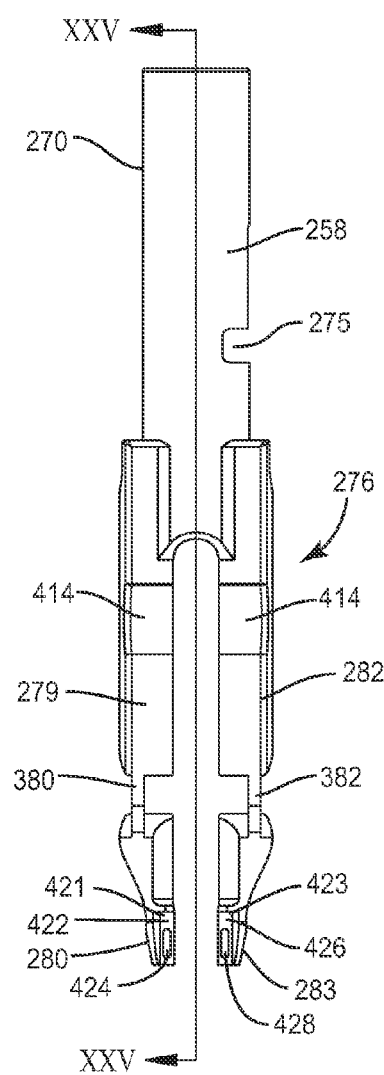
FIG. 23 is a front view of the first arm shown in FIG. 22.
Figure 25:
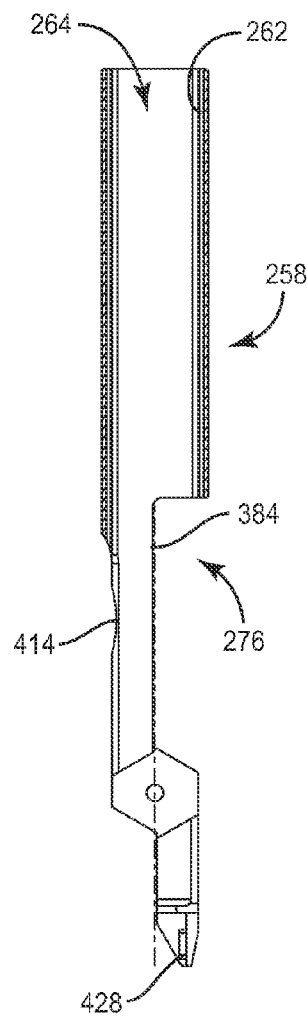
FIG. 25 is a side view of the first arm taken along lines XXV-XXV shown in FIG. 23.
Figure 32:
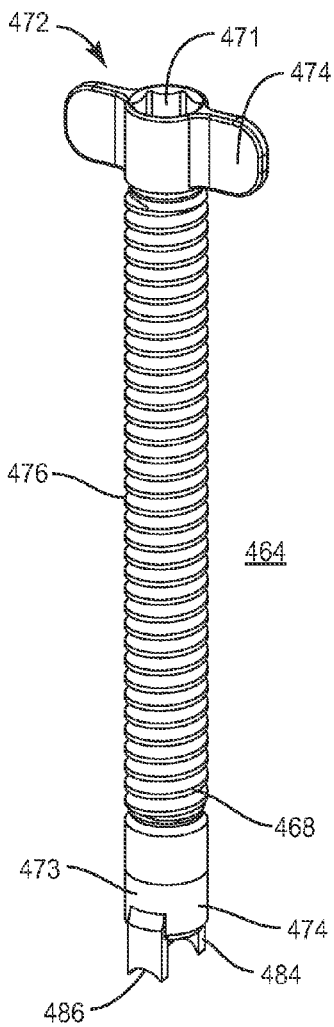
FIG. 32 is a perspective view of one embodiment of the third instrument shown in FIG. 14.
Figure 33:
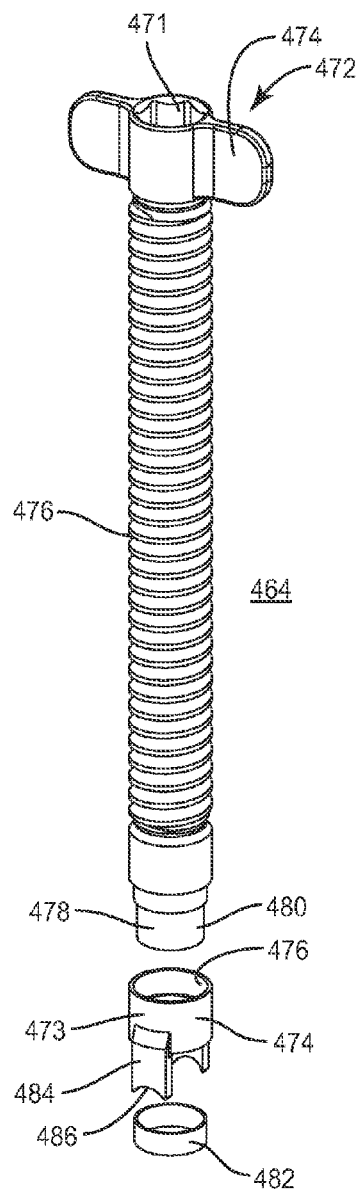
FIG. 33 is a perspective view of the third instrument shown in FIG. 32 with parts separated.
Figure 35:
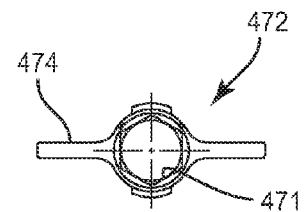
FIG. 35 is an end view of the third instrument shown in FIG. 32.
Figure 34:
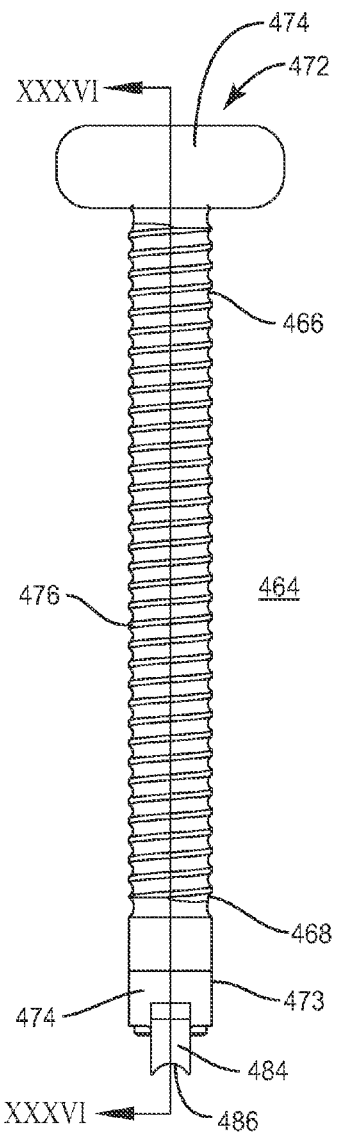
FIG. 34 is a side view of the third instrument shown in FIG. 32.
Figure 37:
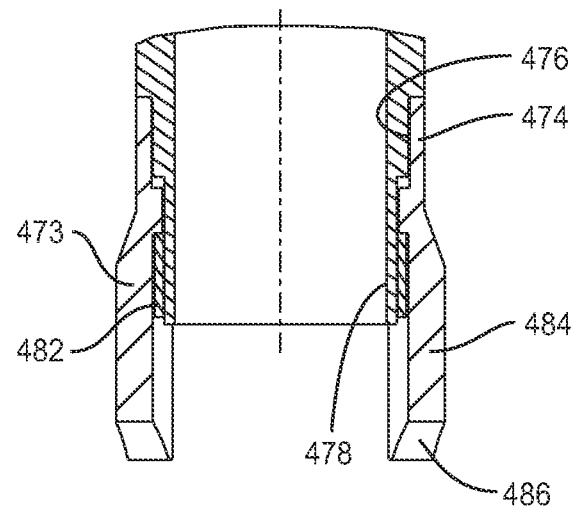
FIG. 37 is an enlarged detail view of the detail of the third instrument shown in FIG. 36.
Figure 36:
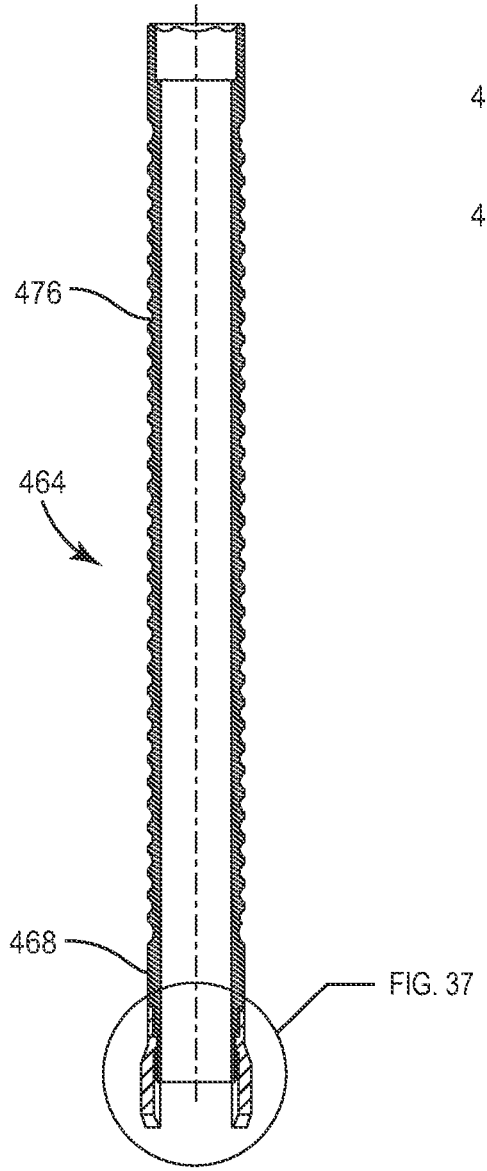
FIG. 36 is a section view of the third instrument shown along lines XXXVI-XXXVI of FIG. 34.
Figure 38:
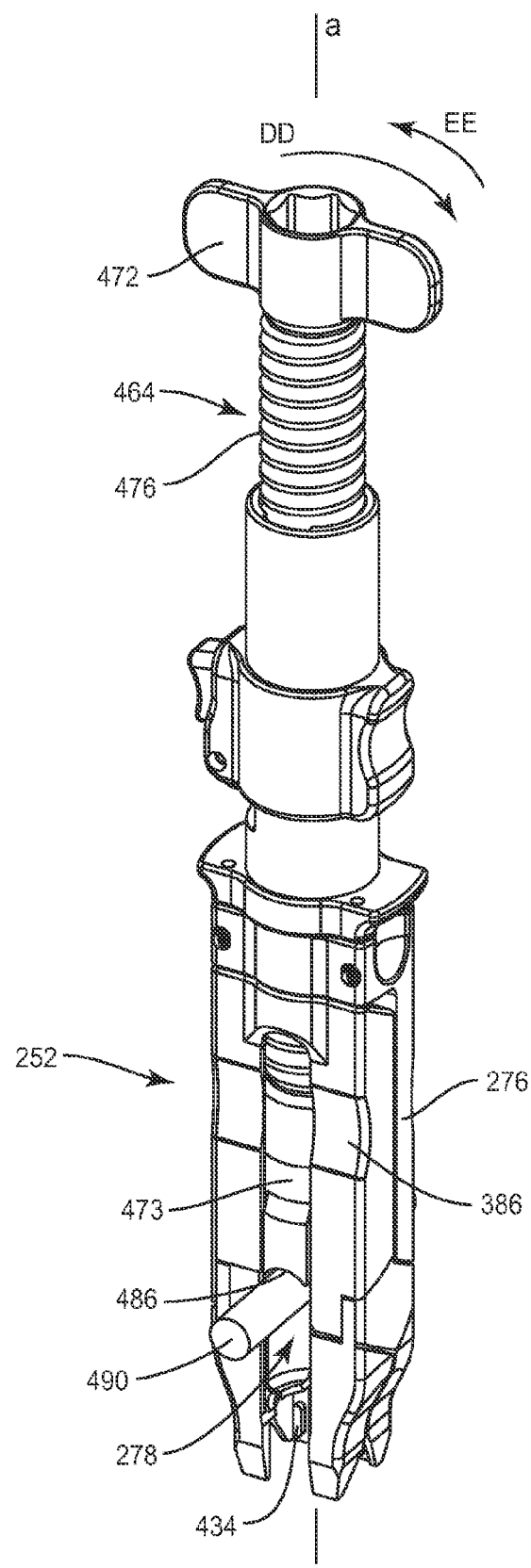
FIG. 38 is a perspective view of the first instrument shown in FIG. 21 and the third instrument shown in FIG. 32 engaging a vertebral construct.

Distal engagement part 280 includes an engagement surface 421 for engaging and capturing bone fastener 130, as shown in FIG. 21. Engagement surface 421 includes an arcuate surface 422 configured to contour and conform to bone faster 130 to facilitate attachment thereto. Engagement surface 421 includes a tab 424 that engages and is received by cavity 134 (FIG. 9) of bone fastener 130 to facilitate releasable fixation of extender 252 with bone fastener 130.

Distal engagement part 283 includes an engagement surface 423 for engaging and capturing bone fastener 130. Engagement surface 423 includes an arcuate surface 426 configured to contour and conform to bone faster 130 to facilitate attachment thereto. Engagement surface 423 includes a tab 428 that engages and is received by cavity 134 of bone fastener 130 to facilitate releasable fixation of extender 252 with bone fastener 130.

Distal engagement part 392 includes an engagement surface 430 for engaging and capturing bone fastener 130. Engagement surface 430 includes an arcuate surface 432 configured to contour and conform to bone faster 130 to facilitate attachment thereto. Engagement surface 430 includes a tab 434 that engages and is received by cavity 134 of bone fastener 130 to facilitate releasable fixation of extender 252 with bone fastener 130.

Distal engagement part 398 includes an engagement surface 436 for engaging and capturing bone fastener 130. Engagement surface 436 includes an arcuate surface 438 configured to contour and conform to bone faster 130 to facilitate attachment thereto. Engagement surface 436 includes a tab 440 that engages and is received by cavity 134 of bone fastener 130 to facilitate releasable fixation of extender 252 with bone fastener 130. This configuration of extender 252 provides a dual sided engagement with bone fastener 130.

In operation of the spinal rod system, extender 252 is oriented for manipulation such that distal engagement parts 392, 398 and 280, 283 are brought into close proximity with a head 132 (FIG. 9) of a bone fastener 130. Engagement surfaces 421, 423, 430, 436 are aligned with extensions 131, 231 of head 132. Tabs 424, 428, 434, 440 are aligned with corresponding receiving cavities 134 of extensions 131, 231 to provide a dual sided engagement.

Instrument release 406 is biased distally by springs on bore 284. It is contemplated that instrument release 406 is permanently connected, such as, for example, by welding, to retainers 288, which are biased by springs in the closed position so instrument release 406 is automatically biased to the closed position. From the open position, grooves 412, 414 are manipulated to move arm 386 to the closed position. The springs are compressed such that retainers 288 engage and move along cam surface 416. Retainers 288 move into retainer bores 286 under spring load. Pivoting arm 386 is pivoted to the closed position and releasably fixed therein such that tabs 424, 428, 434, 440 are received by cavities 134. Distal engagement parts 392, 398 and 280, 283 are disposed in the closed position, as shown in FIG. 21, such that extender 252 surrounds and captures bone fastener 130 in a releasable fixation. To move arm 386 to the open position, instrument release 406 is engaged and manipulated, in the direction shown by arrow CC in FIG. 21, to disengage bone fastener 130.

The spinal rod system includes a second instrument, such as, for example, such as, for example, a reducer 464, as shown in FIGS. 32-37. Reducer 464 extends between a proximal end 466 and a distal end 468. Proximal end 466 includes a handle 472 having a grip surface 474. Handle 472 is manipulable to align reducer 464 with passageway 264. Handle 472 includes a socket cavity 471 for engagement with a tool for rotation thereof. Reducer 464 is disposable in passageway 464 and defines an outer threaded surface 476. Handle 472 is rotated such that surface 476 engages threaded portion 266 of surface 262 to facilitate axial translation of reducer 464 relative to extender 252 along longitudinal axis a.

Distal end 468 includes a pusher 473 that is engageable with a vertebral construct, such as, for example, vertebral rod 490 (FIG. 38) configured for fixation with bone fastener 130 within U-shaped channel 160. Pusher 473 includes a cylindrical flange 474 that defines an aperture 476. Aperture 476 receives a reduced diameter portion 478 for mounting flange 474 with a non-threaded surface 480 of reducer 464. Range 474 is freely slidable about portion 478 such that pusher 473 is rotatable relative to surface 480. A retainer 482 is fixed with portion 478 to retain pusher 473 in the relatively rotatable configuration. Pusher 473 includes legs 484 having arcuate end surfaces 486 configured to engage vertebral rod 490.

Upon positioning and fixation of bone fastener 130 within tissue at a surgical site, according to the requirements of an application, threaded surface 476 is aligned with threaded portion 266. Handle 472 is rotated, in the direction shown by arrows DD in FIG. 38, to translate reducer 464 distally along longitudinal axis a relative to extender 252. Reducer 464 is translated such that arcuate end surfaces 486 engage vertebral rod 490 disposed in rod slot 278 in a configuration to move vertebral rod 490 distally into engagement with bone fastener 130.

Reducer 464 is further translated distally to drive vertebral rod 490 into U-shaped channel 160 (FIG. 9). As reducer 464 is rotated and translates axially, end surfaces 486 maintain alignment with U-shaped channel 160 and reducer 464 continues to rotate relative to pusher 473. As such, end surfaces 486 support vertebral rod 490 in a guided alignment with U-shaped channel 160. Although pusher 473 is rotatable relative to reducer 464, pusher 473 is configured to engage arms 276, 386 to prevent rotation of pusher 473, and vertebral rod 490, relative to arms 276, 386. This configuration maintains alignment of vertebral rod 490 with U-shaped channel 160.

Handle 472 is manipulated to translate reducer 464 and drive vertebral rod 490 into U-shaped channel 160 for fixation with bone fastener 130, according to the requirements of a particular application. Handle 472 is rotatable, in the direction shown by arrows EE in FIG. 38, to translate reducer 464 proximally such that reducer 464 is removed from extender 252. Vertebral rod 490 can be fixedly secured with bone fastener 130 via a set screw (not shown) or similar securement. It is envisioned that the spinal rod system employing extender 252 may include one or a plurality of extenders, inserters, reducers, bone fasteners and/or vertebral constructs, which may be alternately sized and dimensioned, and arranged as a kit, according to the requirements of a particular application. It is further envisioned that the spinal rod system employing extender 252 may be used with various surgical procedures, such as, for example, those described herein.

Figure 39:
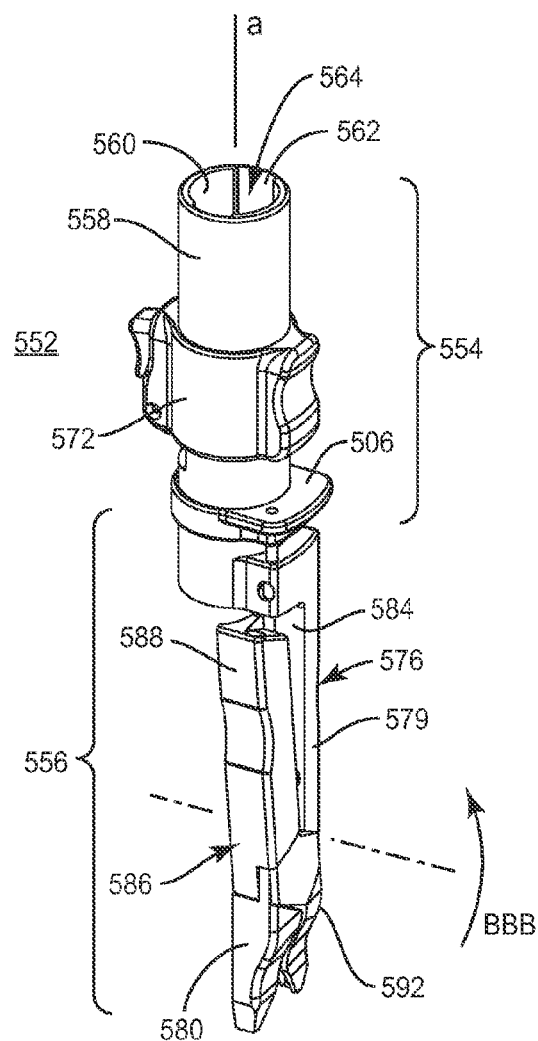
FIG. 39 is a perspective view of one embodiment of the first instrument shown in FIG. 20.
Figure 40:
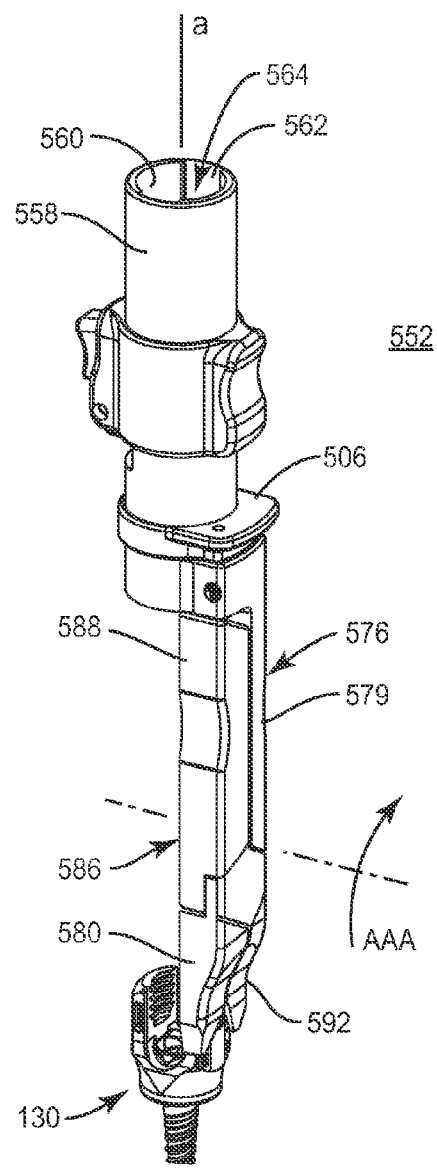
FIG. 40 is a perspective view of the first instrument shown in FIG. 39 engaging a fastener.
Figure 41:
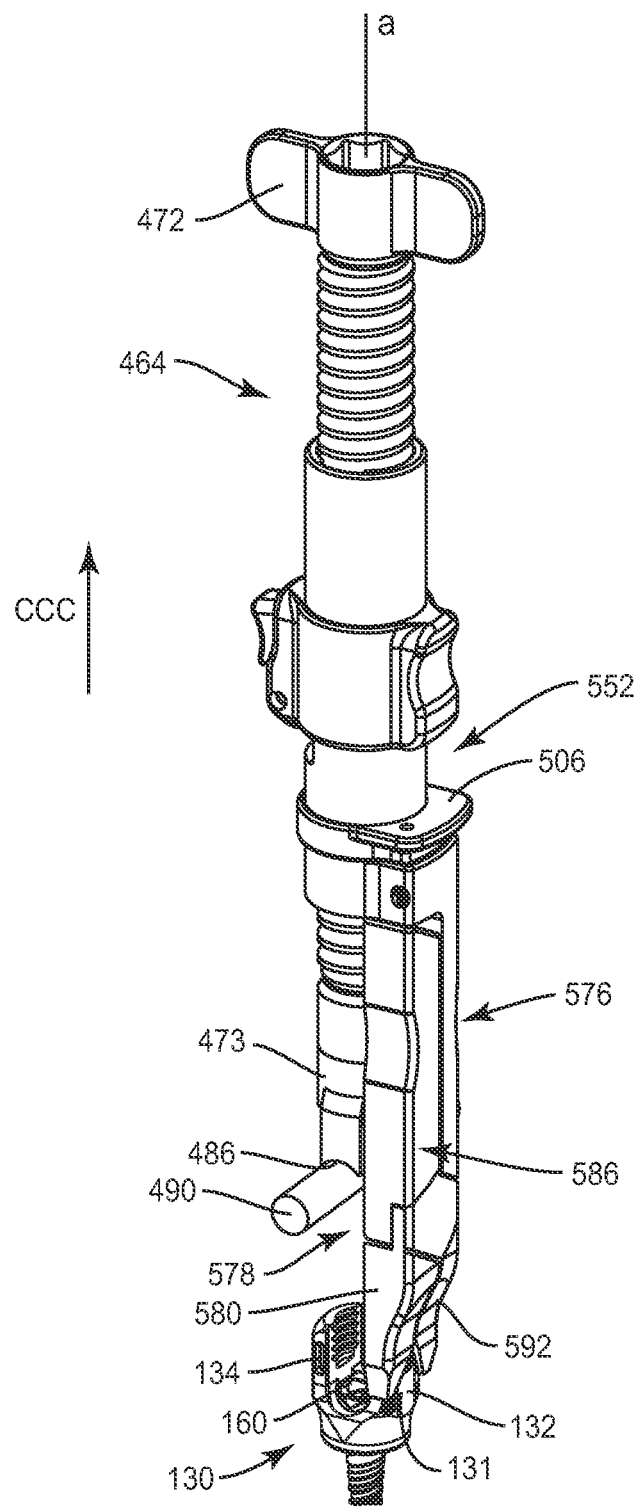
FIG. 41 is a perspective view of the first instrument shown in FIG. 39 engaging a fastener and the third instrument shown in FIG. 32 engaging a vertebral construct.

In one embodiment, as shown in FIGS. 39-41, the spinal rod system, similar to that described with regard to FIGS. 20-38, includes a first instrument, such as, for example, an extender 552 that extends along a longitudinal axis a between a proximal portion 554 and a distal portion 556. Proximal portion 554 includes a tubular body 558 having a cylindrical cross-section configuration and a proximal opening 560. Tubular body 558 includes an inner surface 562, similar to extender 252 described above, which defines a passageway 564 and includes a quick release handle 572.

Distal portion 556 includes a stationary arm 576 extending along longitudinal axis a and defining at least a portion of a rod slot 578 (FIG. 41) disposed in communication with passageway 564. Stationary arm 576 includes a single leg extension 579 that extends to a hinge connection portion and defines a distal engagement part 580. It is contemplated that leg extension 579 may be flexible, jointed and/or articulating.

Stationary arm 576 defines a recess 584 configured for movable disposal of a second arm, such as, for example, a pivoting arm 586 of extender 552. Pivoting arm 586 includes a single leg extension 588 that extends to a hinge connection portion and defines a distal engagement part 592. It is contemplated that leg extension 588 may be flexible, jointed and/or articulating.

Stationary arm 576 is attached to pivoting arm 586 at the hinge connection portions of leg extensions 579, 588. Pivoting arm 586 is pivotable relative to stationary arm 576 such that pivoting arm 586 rotates to capture bone fastener 130 with stationary arm 576 in a releasable fixation to provide a single sided engagement. Pivoting arm 586 is pivotable to a closed position (FIG. 40) such that leg extension 588 and distal engagement part 592 rotate in the direction shown by arrows AAA in FIG. 39. Leg extension 588 and distal engagement part 592 rotate about the hinge connection portions and relative to stationary arm 576 such that distal engagement part 592 captures bone fastener 130 with distal engagement part 580 in a releasable fixation to provide a single sided engagement.

Pivoting arm 586 is pivotable to an open position (FIG. 39) such that leg extension 588 and distal engagement part 592 rotate in the direction shown by arrows BBB in FIG. 39. Leg extension 588 and distal engagement part 592 rotate about the hinge connection portions and relative to stationary arm 576 such that distal engagement parts 592, 580 release bone fastener 130. Pivotal movement of pivoting arm 586 and rotation of pivoting arm 586 relative to stationary arm 576 is configured for single sided capture and facilitated by biasing members, retainers and instrument release components, similar to the structure and operation described with regard to extender 252 described with regard to FIGS. 20-38.

In operation of the spinal rod system, extender 552 is oriented for manipulation such that distal engagement parts 592, 580, similar to the distal engagement parts described above, are brought into close proximity and aligned with head 132 of bone fastener 130. The tabs of distal engagement parts 592, 580 are aligned with corresponding receiving cavities 134 of first extension 131 to provide a single sided engagement.

Instrument release 506 is automatically biased to the closed position, and arms 576, 586 are manipulated such that pivoting arm 586 is moved to the closed position, similar to that described with regard to FIGS. 20-38, such that the tabs of distal engagement parts 592, 580 are received by cavities 134. Distal engagement parts 592, 580 are disposed in the closed position, as shown in FIG. 40, such that extender 552 captures bone fastener 130 in a releasable fixation. To move arm 586 to the open position, instrument release 506 is engaged and manipulated, in the direction shown by arrow CCC in FIG. 41, to disengage bone fastener 130.

Reducer 464, as described with regard to FIGS. 32-37, is aligned with passageway 564. Handle 472 is rotated to translate reducer 464 distally along longitudinal axis a relative to extender 552, as shown in FIG. 41. Reducer 464 is translated such that arcuate end surfaces 486 engage vertebral rod 490 disposed in rod slot 578 in a configuration to move vertebral rod 490 distally into engagement with bone fastener 130.

Reducer 464 is further translated distally to drive vertebral rod 490 into U-shaped channel 160. As reducer 464 is rotated and translates axially, end surfaces 486 maintain alignment with U-shaped channel 160 and reducer 464 continues to rotate relative to pusher 473. As such, end surfaces 486 support vertebral rod 490 in a guided alignment with U-shaped channel 160. Although pusher 473 is rotatable relative to reducer 464, pusher 473 is configured to engage arms 576, 586 to prevent rotation of pusher 473 and vertebral rod 490, relative to arms 576, 586. This configuration maintains alignment of vertebral rod 490 with U-shaped channel 160.

Handle 472 is manipulated to translate reducer 464 and drive vertebral rod 490 into U-shaped channel 160 for fixation with bone fastener 130, according to the requirements of a particular application. Handle 472 is rotatable to translate reducer 464 proximally such that reducer 464 is removed from extender 552. Vertebral rod 490 can be fixedly secured with bone fastener 130 via a set screw (not shown) or similar securement. It is envisioned that the spinal rod system employing extender 552 may include one or a plurality of extenders, inserters, reducers, bone fasteners and/or vertebral constructs, which may be alternately sized and dimensioned, and arranged as a kit, according to the requirements of a particular application. It is further envisioned that the spinal rod system employing extender 552 may be used with various surgical procedures, such as, for example, those described herein.

Figure 42:
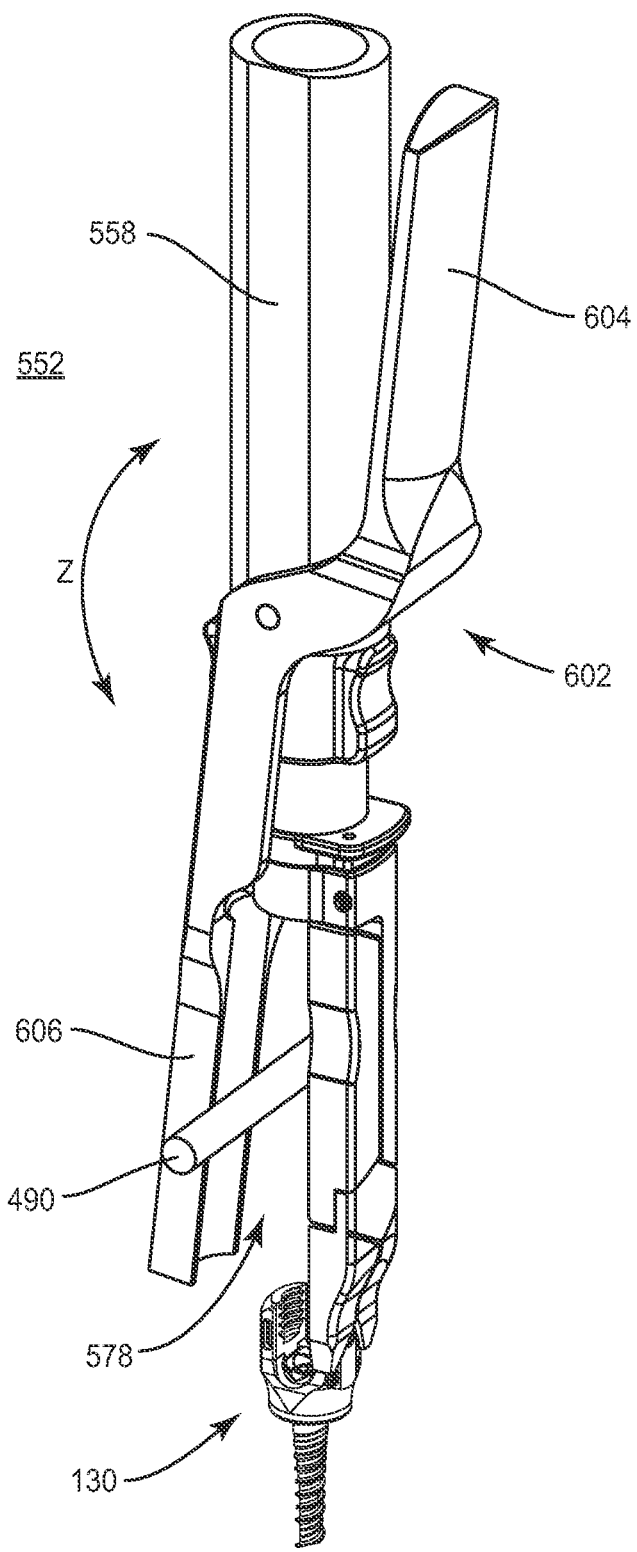
FIG. 42 is a perspective view of the first instrument shown in FIG. 39 engaging a fastener and one embodiment of a handle.
Figure 44:
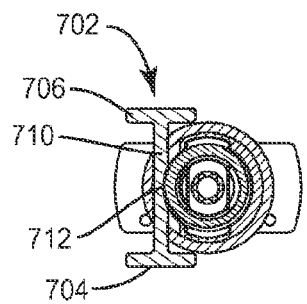
FIG. 44 is an end section view of the system shown along lines XLIV-XLIV of FIG. 43.
Figure 43:
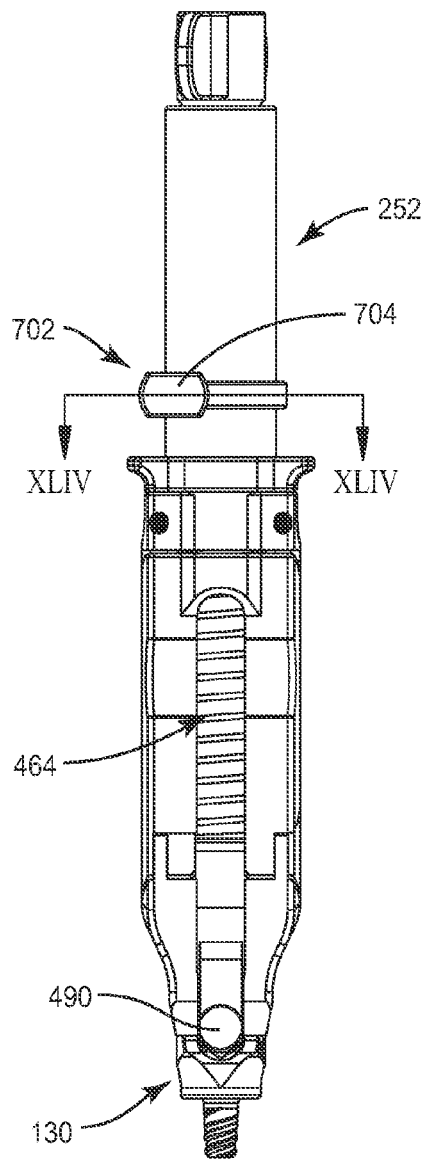
FIG. 43 is a front view of the system shown in FIG. 38 including one embodiment of a quick release locking system engaging a fastener and a vertebral construct.

In one embodiment, as shown in FIG. 42, the spinal rod system, similar to that described above, includes a lateral translation handle 602 mounted with extender 552, as described with regard to FIGS. 39-41. Handle 602 is pivotally attached with body 558 and has a grip surface 604 for manipulation thereof. Handle 602 extends to an engagement member 606 configured to capture vertebral rod 490. Grip surface 604 is manipulable to rotate engagement member 606, in the direction shown by arrows Z, to engage and capture vertebral rod 490. Engagement member 606 guides vertebral rod 490 into rod slot 578.

In one embodiment, as shown in FIGS. 43-47, the spinal rod system, similar to that described above, includes a quick release locking system 702, similar the quick release handle described with regard to FIGS. 20-38. Quick release locking system 702 includes a locking element 704, which is mounted with an outer surface of extender 252 (FIGS. 20-38) for engaging and releasing a reducer 264 (FIGS. 32-37). The inner surface of extender 252, for the purposes of this embodiment, is non-threaded and the threads of reducer 264 do not engage such inner surface to facilitate axial translation thereof.

Figure 45:
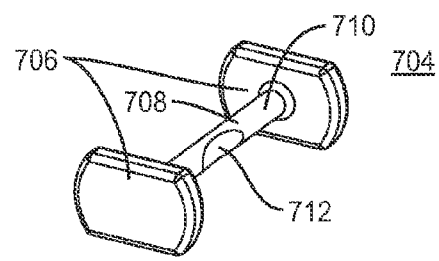
FIG. 45 is a perspective view of a locking element shown in FIG. 43.

Locking element 704, as shown in FIG. 45, includes enlarged end portions 706 configured to engage the outer surface of extender 252 for mounting therewith. End portions 706 are connected by a cylindrical shaft 708 that defines a circumferential outer surface 710. Outer surface 710 defines a centrally disposed notch 712 extending about only a quadrant of the entire circumferential outer surface 710. Notch 712 has a concave configuration such that the remaining portion of surface 710 is arcuate. Notch 712 provides an interruption within the uniformity of outer surface 710.

Figure 47:
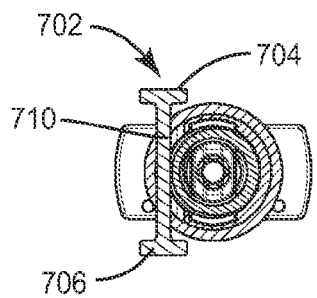
FIG. 47 is an end section view of the system shown along lines XLVII-XLVII of FIG. 46.
Figure 46:
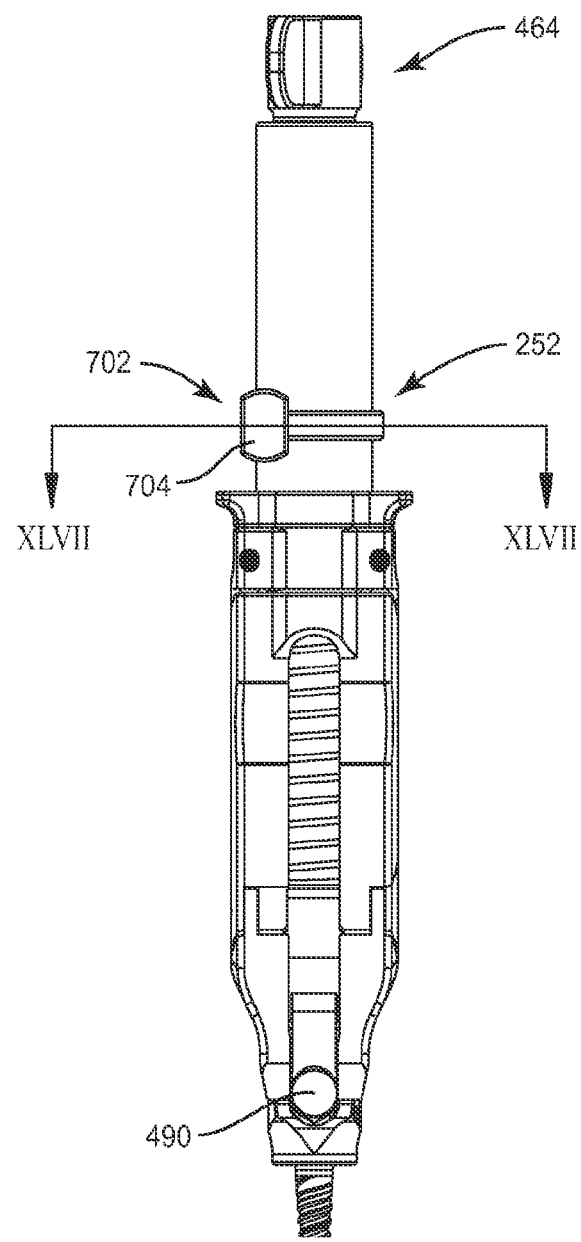
FIG. 46 is a front view of the system shown in FIG. 43.

Locking element 704 is rotatable between a disengaged position of quick release locking system 702 (FIGS. 43-44) and an engaged position of quick release locking system 702 (FIGS. 46-47). In the disengaged position, notch 712 is aligned with the threads of reducer 464 such that reducer 464 is not disposed in a mating, threaded engagement shaft 708. Reducer 464 can slide freely into engagement with vertebral rod 490. In the engaged position, end portions 706 are manipulated and rotated relative to extender 252, such that shaft 708 is rotated a quarter turn and notch 712 is rotated out of alignment with the threads of reducer 464. At least a portion of the remaining circumferential portion of surface 710 is aligned with the threads of reducer 464. As such, the threads of reducer 464 are disposed in a mating, threaded engagement shaft 708. Rotation of reducer 464 facilitates translation of reducer 464 relative to extender 252, as described.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal rod system comprising:
   at least one first instrument extending between a proximal portion and a distal portion along a longitudinal axis thereof, the proximal portion defining an inner cavity extending along the longitudinal axis,
   the at least one first instrument including at least one first arm extending along the longitudinal axis, the at least one first arm includes a first leg extension and a second leg extension, the first and second leg extension each including a tapered slot and a distal inner surface having a tapered configuration,
   the at least one first arm defining at least a portion of a vertebral construct cavity disposed in communication with the inner cavity and including a distal end being configured to engage a bone fastener;
   an actuator arm movable along the longitudinal axis and comprising a distal head that tapers distally to an increased width, the distal head being engageable with the distal inner surfaces to move the at least one first arm in a direction transverse to the longitudinal axis between a first position and a second position such that the distal end of the at least one first arm engages the bone fastener; and
   a slide disposed with a slot at a distal end of the actuator arm to fix the slide axially relative to the actuator arm, the slide having enlarged end portions movably disposed in the tapered slots,
   wherein the actuator arm comprises an elongated portion including an aperture, the at least one first instrument comprising a pin that is received in the aperture to connect the actuator arm with a handle, the pin extending through inner and outer surfaces of the handle.

2. The spinal rod system of claim 1, wherein the leg extensions defining an arm cavity therebetween.

3. The spinal rod system of claim 1, wherein the at least one first instrument further includes an actuator engageable with the at least one first arm to move the at least one first arm between the first position and the second position such that the distal end of the at least one first arm engages the bone fastener.

4. The spinal rod system of claim 1, wherein the leg extensions define an arm cavity configured for relative movement of the actuator arm therein.

5. The spinal rod system of claim 1, wherein the first leg extension defines a distal engagement part and the second leg extension defines a distal engagement part, the leg extensions defining an arm cavity configured for relative movement of the actuator arm therein.

6. The spinal rod system of claim 1, wherein the slide engages a proximal first end of each of the tapered slots when the at least one arm is in the second position to limit movement of the actuator arm.

7. The spinal rod system of claim 1, wherein the handle includes a grip surface configured to facilitate axial movement of the actuator arm.

8. The spinal rod system of claim 1, wherein the at least one first arm includes a first arm and a second arm extending along the longitudinal axis, the first arm and the second arm being disposed in opposed relation to define the vertebral construct cavity.

9. The spinal rod system of claim 8, wherein the at least one first instrument further includes a first actuator engageable with the first arm to move the first arm between a first position and a second position such that the distal end of the first arm engages a bone fastener, and a second actuator engageable with the second arm to move the second arm between a first position and a second position such that the distal end of the first arm engages a bone fastener.

10. The spinal rod system of claim 1, wherein the slide is removably disposed in a slot of the actuator arm that extends transverse to an axis defined by the actuator arm.

11. The spinal rod system of claim 1, wherein the vertebral construct cavity is defined by a first wall of the at least one first arm that extends parallel to the longitudinal axis and a second wall of the distal portion that extends transverse to the longitudinal axis.

12. The spinal rod system of claim 1, wherein the at least one first arm is biased to the second position.

13. The spinal rod system of claim 1, wherein:
   the spinal rod system comprises the bone fastener, the bone fastener comprising first and second extensions each comprising a pair of receiving cavities; and
   the first and second leg extensions each include an engagement surface configured to engage the first extension, the engagement surfaces each comprising a tab projecting therefrom, the tabs being spaced apart from the receiving cavities of the first extension when the at least one first arm is in the first position and the tabs being disposed in the receiving cavities of the first extension when the at least one first arm is in the second position.

14. The spinal rod system of claim 13, wherein the engagement surfaces each include an arcuate surface configured to contour and conform to the first extension to facilitate attachment thereto.

15. A spinal rod system comprising:

at least one first instrument extending between a proximal portion and a distal portion along a longitudinal axis thereof, the proximal portion defining an inner cavity extending along the longitudinal axis, the at least one first instrument including at least one first arm extending along the longitudinal axis, the at least one first arm includes a first leg extension and a second leg extension, the first and second leg extension each including a tapered slot and a distal inner surface having a tapered configuration, the at least one first arm defining at least a portion of a vertebral construct cavity disposed in communication with the inner cavity and including a distal end being configured to engage a bone fastener;

an actuator arm movable along the longitudinal axis and comprising a distal head that tapers distally to an increased width, the distal head being engageable with the distal inner surfaces to move the at least one first arm in a direction transverse to the longitudinal axis between a first position and a second position such that the distal end of the at least one first arm engages the bone fastener; and a slide disposed with a slot at a distal end of the actuator arm to fix the slide axially relative to the actuator arm, the slide having enlarged end portions movably disposed in the tapered slots, wherein the distal head includes an aperture, the at least one first instrument comprising a pin disposed in the aperture to connect the actuator arm with the first and second leg extensions, wherein the pin engages the slide.

* * * * *